US009757369B2

(12) United States Patent
Martinez Gil et al.

(10) Patent No.: US 9,757,369 B2
(45) Date of Patent: Sep. 12, 2017

(54) HETEROCYCLIC GSK-3 ALLOSTERIC MODULATORS

(71) Applicant: Consejo Superior de Investigaciones Cientificas (CSIC), Madrid (ES)

(72) Inventors: Ana Martinez Gil, Madrid (ES); Carmen Gil Ayuso-Gontan, Madrid (ES); Valle Palomo Ruiz, Madrid (ES); Concepcion Perez Martin, Madrid (ES); Daniel I. Perez Fernandez, Madrid (ES); Julio Alberto Reyes Rodriguez, Madrid (ES)

(73) Assignee: Consejo Superior de Investigaciones Cientificas (CSIC), Madrid (ES)

( * ) Notice: Subject to any disclaimer, the term of this patent is extended or adjusted under 35 U.S.C. 154(b) by 0 days.

(21) Appl. No.: 15/415,188

(22) Filed: Jan. 25, 2017

(65) Prior Publication Data

US 2017/0196850 A1 Jul. 13, 2017

Related U.S. Application Data

(62) Division of application No. 14/920,030, filed on Oct. 22, 2015, now Pat. No. 9,585,879, which is a division of application No. 14/348,277, filed as application No. PCT/ES2012/070672 on Sep. 28, 2012, now Pat. No. 9,193,688.

(30) Foreign Application Priority Data

Sep. 30, 2011 (ES) .................................. 201131582

(51) Int. Cl.
C07D 215/56 (2006.01)
A61K 31/4704 (2006.01)

(52) U.S. Cl.
CPC ................ A61K 31/4704 (2013.01)

(58) Field of Classification Search
None
See application file for complete search history.

(56) References Cited

U.S. PATENT DOCUMENTS

2009/0325948 A1 12/2009 Hurley et al.

FOREIGN PATENT DOCUMENTS

WO 2006091246 A1 8/2006
WO 2007106537 A2 9/2007

OTHER PUBLICATIONS

Eglen, Richard et al, "Drug Discovery and the Human Kinome: Recent Trends", Elsevier, Pharmacology & Therapeutics 130, (2011) pp. 144-156.
Martinez, Ana, "Preclinical Efficacy on GSK-3 Inhibitors: Towards a Future Generation of Powerful Drugs" NeuroPharma, Madrid Spain, vol. 28, No. 5, pp. 773-796 (2008).
McInnes, Campbell et al, "Strategies for the Design of Potent and Selective Kinase Inhibitors", Current Pharmaceutical Design, 2005, 11, pp. 1845-1863.
Martinez, Ana et al, "Glycogen Synthase Kinase 3 Inhibitors in the Next Horizon for Alzheimer's Disease Treatment", SAGE-Hindaw Access to Research, International Journal of Alzheimer's Disease, vol. 011 Article ID 280502, 7 pages.
Embi, Noor et al, "Glycogen Synthase Kinase-3 from Rabbit Skeletal Muscle", Eur. J. Biochem, 107, (1980) pp. 519-527.
Phukan, S et al, "GSK3B: Role in Therapeutic Landscape and Development of Modulators", British Journal of Pharmacolony (2010), 160, pp. 1-19.
Lu, J. et al, "In vitro and in vivo activities of a new lead compound 12906 against micobacterium tuberculosis", Pharmacology, 2010, vol. 85, pp. 366-371.
Deng, J. et al, "Discovery of Novel Anticancer Compounds based on a quinoxiline idrazine pharmacophore", Chem Med Chem 2008, vol. 3, pp. 1677-1686.
Valle, P. et al, "Exploring the binding sites of glycogen synthase kinase 3, Identification and Characterization of Allosteric Modulation Cavities", Journal of Medicinal Chemistry, Nov. 3, 2011, vol. 54, pp. 8461-8470.
Kannoji, Akanksha et al, "GSK3B: A master switch and a promising target", informa healthcare, 2008, pp. 1443-1455.
Trillo, "Generalities About Medicinal Preparations for Oral Administration: Classification", Treatise on Galenic Pharmacy, Farmacia 2000, 12 pages.

*Primary Examiner* — Timothy R Rozof
(74) *Attorney, Agent, or Firm* — Hayes Soloway PC (57) ABSTRACT

The present invention relates to heterocyclic substituted quinoline derivatives as allosteric inhibitors of the glycogen synthase kinase-3 (GSK-3) enzyme. Therefore, these compounds are useful for the manufacturing of a medicament designed for the treatment and/or prevention of diseases wherein GSK-3 is involved, such as neurodegenerative diseases, inflammatory diseases, cancer, diabetes, and to promote various regenerative processes.

9 Claims, 2 Drawing Sheets

HETEROCYCLIC GSK-3 ALLOSTERIC MODULATORS

CROSS REFERENCE TO RELATED APPLICATIONS

This application is a divisional of U.S. application Ser. No. 14/920,030 filed on Oct. 22, 2015, which itself is a divisional of U.S. application Ser. No. 14/348,277 filed on Jul. 18, 2014, now U.S. Pat. No. 9,193,688, which itself is a 371 of International Application Serial No. PCT/ES2012/070672 filed on Sep. 28, 2012, which claims priority of Spanish Application Serial No. ES P201131582 filed on Sep. 30, 2011, each of which this application claims benefit from and the contents of which are hereby incorporated by reference.

DESCRIPTION

The present invention relates to heterocyclic substituted quinoline derivatives as allosteric inhibitors of the glycogen synthase kinase-3 (GSK-3) enzyme. Therefore, these compounds are useful for the manufacturing of a medicament designed for the treatment and/or prevention of diseases wherein GSK-3 is involved, such as neurodegenerative diseases, inflammatory diseases, cancer and diabetes, as well as to promote various regenerative processes. Therefore, the invention may be included within the field of pharmaceutical chemistry.

STATE OF THE ART

Glycogen synthase kinase-3 (GSK-3) is an enzyme of the kinase family which catalyses the phosphorylation of serine or threonine residues in various substrates. It was originally discovered due to its role in glycogen biosynthesis, after which it is named [Rylatt, D. B.; Aitken, A.; Bilham, T.; Condon, G. D.; Embi, N.; Cohen, P. Glycogen Synthase Kinase 3 from rabbit skeletal muscle. Separation from cyclic-AMP-dependent protein kinase and, phosphorylase kinase. Eur J Biochem. 1980 107, 519-527]. This enzyme plays a key role in several cell signalling pathways, including Wnt pathways, the cell division cycle, inflammation, cell proliferation, DNA damage response, cell death and survival, and neuronal differentiation, amongst others [Phukan, S.; Babu, V. S.; Kannoji, A.; Hariharan, R.; Balaji, V. N. GSK3beta: role in therapeutic landscape and development of modulators. Br. J. Pharmacol. 2010, 160, 1-19]. Recently, it has been demonstrated that an overexpression/overactivation of GSK-3 is sufficient to induce neuronal cell death, and is related to various pathologies, such as bipolar disorders, neurodegenerative diseases, especially Alzheimer's disease, type II diabetes and chronic inflammatory diseases [Kannoji, A., Phukan, S., Sudher, V., Balaji, V. N. "GSK3beta: a master switch and a promising target". Expert Opin Ther Targets. 2008, 12, 1443-1455].

In recent years, numerous GSK-3 inhibitors have been synthesised, which are promising molecules for the treatment of various diseases, such as diabetes, cancer and neurodegenerative diseases [Martinez, A. Preclinical efficacy on GSK-3 inhibitors: towards a future generation of powerful drugs. Med. Res. Rev. 2008, 28, 773-796]. However, given that the human kinome is composed of more than 500 kinases with a high identity at the catalytic site, i.e. the ATP-binding site, the discovery and/or design of specific inhibitors of a given kinase is an open challenge. One of the possibilities of increasing the selectivity of kinases lies in the design of allosteric modulators [Eglen, R.; Reisine, T. Drug discovery and the human kinome: recent trends. Pharmacol. Ther. 2011, 130, 144-156]. These compounds generally bind to unique, specific regions of the kinase, inducing conformational changes, and are very useful when resistances caused by the inhibitors that compete with adenosine triphosphate (ATP) appear [McInnes, C.; Fischer, P. M. Strategies for the design of potent and selective kinase inhibitors. Curr. Pharm. Des. 2005, 11, 1845-1863]. Moreover, allosteric modulators provide mild modulation of the corresponding enzyme, which is particularly important in the inhibition of GSK-3 [Martinez, A., Gil, C., Perez, D. I. Glycogen synthase kinase 3 inhibitors in the next horizon for Alzheimer's disease treatment. Int. J. Alzheimer's Dis. 2011, doi: 10.406/2011/280502]. In this case, only the aberrant overexpression/overactivation of GSK-3 must be inhibited in order to treat the pathologies wherein this kinase is involved.

DETAILED DESCRIPTION OF THE INVENTION

The present invention presents a family of compounds, and the method for obtaining them, that have the capacity to inhibit the GSK-3 enzyme in the micromolar range. The kinetic studies of GSK-3 inhibition presented here show that these compounds are allosteric GSK-3 inhibitors. On the other hand, these compounds are capable of reducing inflammation in the cellular models presented herein.

A first aspect of the present invention relates to the use of a compound with the formula (I)

Formula (I)

or the salts, solvates or stereoisomers thereof, where $R_1$ is selected from H, an optionally substituted $C_1$-$C_5$ alkyl group, an optionally substituted $C_2$-$C_5$ alkenyl group, $R_2$ is an optionally substituted $C_5$-$C_{15}$ alkyl group, $R_3$ is selected from H, halogen, an optionally substituted $C_1$-$C_5$ alkyl group or an optionally substituted $C_1$-$C_5$-(O)-alkyl group, n is a value between 1 and 4, $R_4$, $R_5$ and $R_6$ are independently selected from H or an optionally substituted $C_1$-$C_5$ alkyl group, provided that, when $R_1$ is ethyl or H and $R_3$, $R_4$, $R_5$ and $R_6$ are H, $R_2$ cannot be heptyl, for the manufacturing of a medicament for the treatment and/or prevention of a disease selected from neurodegenerative diseases, inflammatory diseases, cancer, diabetes, or to promote regenerative processes.

In the present invention, the term "alkyl" refers to linear or branched hydrocarbonated chain radicals, with between 1 and 15 carbon atoms, which bind to the rest of the molecule by means of a single bond, for example, propyl, ethyl, methyl, isopropyl, undecanoyl, heptadecanoyl, octadecanoyl, etc. These alkyl radicals may be optionally substituted in one or more positions by one or more groups, such as cycloalkyl, hydroxyl, amines, amides, oxo, cyano, halogens, aryl, etc.

In the present invention, the term "cycloalkyl" refers to cyclic hydrocarbonated chain radicals, preferably with between 3 and 6 carbon atoms, and more preferably 3, totally or partially saturated, and formed by only carbon and hydrogen atoms, such as cyclopropyl, cyclopentyl or cyclohexyl, and which may be optionally substituted by one or more groups, such as alkyl, halogens, hydroxyl, amines, amides, cyano, etc.

In the present invention, the term "alkenyl" refers to linear or branched hydrocarbonated chain radicals, which contain one or more double carbon-carbon bonds, for example, vinyl, 1-propenyl, allyl, isoprenyl, 2-butenyl, 1,3-butadienyl, etc. The alkenyl radicals may be optionally substituted by one or more groups, such as halogen, hydroxyl, carboxyl, cyano, carbonyl, acyl, amino, nitro, etc.

In the present invention, the term "aryl" refers to single or multiple aromatic rings, which have between 5 and 18 links wherefrom a proton has been eliminated from the ring. Preferably, the aryl group has between 5 and 7 carbon atoms. Aryl groups are, for example, without being limited thereto, phenyl, naphthyl, diphenyl, indenyl, phenanthryl or anthracyl. The aryl radicals may be optionally substituted by one or more substituents, such as alkyl, hydroxyl, amines, amide, cyano, halogens, etc.

"Halogen" refers to fluorine, chlorine, bromine or iodine.

In a preferred embodiment of the present invention, $R_4$, $R_5$ and $R_6$ are H.

In another preferred embodiment of the present invention, $R_1$ is H or a $C_1$-$C_3$ alkyl group; more preferably, $R_1$ is H, optionally substituted methyl, ethyl or isobutyl. In a more preferred embodiment, $R_1$ is a methyl group substituted by a cycloalkyl, preferably cyclopropyl, or an aryl, preferably phenyl.

In another preferred embodiment of the present invention, $R_2$ is a $C_7$-$C_{11}$ alkyl group; more preferably, $R_2$ is a $C_7$ alkyl group or a $C_{11}$ alkyl group.

In the compound with the formula (I) of the invention, when $R_3$ is a halogen group, it is preferably Br, Cl or F, and, more preferably, n is 1.

In the compound with the formula (I) of the invention, when $R_3$ is H, n is preferably 4.

A more preferred embodiment relates to the use of a compound selected from the following group:
4-Hydroxy-1-methyl-N'-octanoyl-2-oxo-1,2-dihydroquinoline-3-carbohydrazide (3)
N'-Dodecanoyl-4-hydroxy-1-methyl-2-oxo-1,2-dihydroquinoline-3-carbohydrazide (4)
N'-Dodecanoyl-1-ethyl-4-hydroxy-2-oxo-1,2-dihydroquinoline-3-carbohydrazide (6)
N'-Dodecanoyl-4-hydroxy-2-oxo-2-hydroquinoline-3-carbohydrazide (13)
7-Chloro-4-hydroxy-N'-octanoyl-2-oxo-2-hydroquinoline-3-carbohydrazide (14)
7-Chloro-N'-dodecanoyl-4-hydroxy-2-oxo-2-hydroquinoline-3-carbohydrazide (15)
6-Fluoro-N'-dodecanoyl-4-hydroxy-2-oxo-2-hydroquinoline-3-carbohydrazide (17)
4-Hydroxy-1-(isoprenyl)-N'-octanoyl-2-oxo-1,2-dihydroquinoline-3-carbohydrazide (42)
N'-Dodecanoyl-4-hydroxy-1-(isoprenyl)-2-oxo-1,2-dihydroquinoline-3-carbohydrazide (43)
N'-Dodecanoyl-4-hydroxy-1-isobutyl-2-oxo-1,2-dihydroquinoline-3-carbohydrazide (44)
1-(Cyclopropylmethyl)-N'-dodecanoyl-4-hydroxy-2-oxo-1,2-dihydroquinoline-3-carbohydrazide (45)
1-Benzyl-N'-dodecanoyl-4-hydroxy-2-oxo-1,2-dihydroquinoline-3-carbohydrazide (46)
6-Bromo-N'-dodecanoyl-4-hydroxy-2-oxo-2-hydroquinoline-3-carbohydrazide (47)
6-Chloro-N'-dodecanoyl-4-hydroxy-2-oxo-2-hydroquinoline-3-carbohydrazide (48)
6-Bromo-4-hydroxy-1-methyl-N'-octanoyl-2-oxo-1,2-dihydroquinoline-3-carbohydrazide (49)
6-Bromo-N'-dodecanoyl-4-hydroxy-1-methyl-2-oxo-1,2-dihydroquinoline-3-carbohydrazide (50)
6-Bromo-1-ethyl-4-hydroxy-N'-octanoyl-2-oxo-1,2-dihydroquinoline-3-carbohydrazide (51)
6-Bromo-N'-dodecanoyl-1-ethyl-4-hydroxy-2-oxo-1,2-dihydroquinoline-3-carbohydrazide (52)
6-Chloro-4-hydroxy-1-methyl-N'-octanoyl-2-oxo-1,2-dihydroquinoline-3-carbohydrazide (53)
6-Chloro-N'-dodecanoyl-4-hydroxy-1-methyl-2-oxo-1,2-dihydroquinoline-3-carbohydrazide (54)
6-Chloro-1-ethyl-4-hydroxy-N'-octanoyl-2-oxo-1,2-dihydroquinoline-3-carbohydrazide (55)
6-Chloro-N'-dodecanoyl-1-ethyl-4-hydroxy-2-oxo-1,2-dihydroquinoline-3-carbohydrazide (56)
7-Chloro-4-hydroxy-1-methyl-N'-octanoyl-2-oxo-1,2-dihydroquinoline-3-carbohydrazide (57)
7-Chloro-N'-dodecanoyl-4-hydroxy-1-methyl-2-oxo-1,2-dihydroquinoline-3-carbohydrazide (58)
7-Chloro-1-ethyl-4-hydroxy-N'-octanoyl-2-oxo-1,2-dihydroquinoline-3-carbohydrazide (59)
7-Chloro-N'dodecanoyl-1-ethyl-4-hydroxy-2-oxo-1,2-dihydroquinoline-3-carbohydrazide (60)
1-Benzyl-7-chloro-4-hydroxy-N'-octanoyl-2-oxo-1,2-dihydroquinoline-3-carbohydrazide (61)
1-Benzyl-7-chloro-N'dodecanoyl-4-hydroxy-2-oxo-1,2-dihydroquinoline-3-carbohydrazide (62)
N',1-Dibenzyl-N'-dodecanoyl-4-hydroxy-2-oxo-1,2-dihydroquinoline-3-carbohydrazide (63)

Another preferred embodiment relates to the use of a compound selected from the following group:
N'-Dodecanoyl-1-ethyl-4-hydroxy-2-oxo-1,2-dihydroquinoline-3-carbohydrazide (4)
7-Chloro-N'-dodecanoyl-4-hydroxy-2-oxo-2-hydroguinoline-3-carbohydrazide (15)
6-Bromo-N'-dodecanoyl-4-hydroxy-2-oxo-2-hydroguinoline-3-carbohydrazide (47)
6-Chloro-N'-dodecanoyl-4-hydroxy-2-oxo-2-hydroguinoline-3-carbohydrazide (48)
6-Bromo-N'-dodecanoyl-1-ethyl-4-hydroxy-2-oxo-1,2-dihydroquinoline-3-carbohydrazide (52)
6-Chloro-N'-dodecanoyl-1-ethyl-4-hydroxy-2-oxo-1,2-dihydroquinoline-3-carbohydrazide (56)
7-Chloro-N'-dodecanoyl-4-hydroxy-1-methyl-2-oxo-1,2-dihydroquinoline-3-carbohydrazide (58)
7-Chloro-N'dodecanoyl-1-ethyl-4-hydroxy-2-oxo-1,2-dihydroquinoline-3-carbohydrazide (60)
or the salts, solvates or stereoisomers thereof, for the manufacturing of a medicament designed for the treatment and/or prevention of a disease selected from neurodegenerative diseases, inflammatory diseases, cancer, diabetes, or to promote regenerative processes.

The compounds of the present invention, both those with the general formula (I) and those with the general formula (II), are allosteric GSK-3 inhibitors; therefore, these compounds are used for the treatment and/or prevention of diseases wherein this enzyme is involved. Allosteric inhibitors produce milder modulation of enzymes than competitive inhibitors, with IC50 values in the micromolar range. The GSK-3 enzyme is involved in multiple cell signalling pathways; for this reason, inhibitors of this enzyme aimed at a specific pathway related to a specific pathology end up affecting other pathways, thereby generating undesirable secondary effects. Allosteric modulation of GSK-3 entails a lower impact on those pathways not related to the disease to be treated, which would minimise secondary effects in a patient.

The neurodegenerative diseases may be selected from the list that comprises, without being limited thereto, Alzheimer's disease, Parkinson's disease, amyotrophic lateral sclerosis, cerebral ischaemia, post-encephalitic Parkinsonisms, dystonias, Tourette syndrome, periodic limb movement pathologies, restless legs syndrome, attention deficit hyperactivity disorders, Huntington's disease, progressive supranuclear palsy, Pick's disease, fronto-temporal dementia or neuromuscular diseases.

The inflammatory diseases may be selected, without being limited thereto, from Crohn's disease, ulcerative colitis, rheumatoid arthritis, atherosclerosis, vasculitis or multiple sclerosis.

The cancer may be selected, without being limited thereto, from glioblastoma, leukaemias, lymphomas, or lung, breast, prostate or colon cancer.

The diabetes may be non-insulin-dependent type II diabetes.

Preferably, in the regenerative process to be promoted by the use of compounds with the formula (I), the differentiation of the following stem cells is involved: nervous system stem cells, haematopoietic system stem cells, skeletal system stem cells or myocardial stem cells.

Another aspect of the present invention relates to a compound with the formula (II):

or the salts, solvates or stereoisomers thereof, where $R_1$ is selected from H or an optionally substituted $C_1$-$C_5$ alkyl group or an optionally substituted $C_2$-$C_5$ alkenyl group, $R_2$ is an optionally substituted $C_5$-$C_{15}$ alkyl group, $R_3$ is a halogen, n is a value between 1 and 4, $R_4$, $R_5$ and $R_6$ are independently selected from H or an optionally substituted $C_1$-$C_5$ alkyl group.

In a preferred embodiment of the compounds of the present invention, $R_4$, $R_5$ and $R_6$ are H.

In another preferred embodiment of the compounds of the present invention, $R_1$ is H or a $C_1$-$C_3$ alkyl group, preferably optionally substituted methyl, ethyl or isobutyl.

In a more preferred embodiment, $R_1$ is a methyl group substituted by a cycloalkyl, preferably cyclopropyl, or an aryl, preferably phenyl.

In another more preferred embodiment, $R_1$ is H.

In another preferred embodiment of the compounds of the present invention, $R_2$ is a $C_7$-$C_{11}$ alkyl group; more preferably, $R_2$ is a $C_7$ alkyl group or a $C_{11}$ alkyl group.

In another preferred embodiment, $R_3$ is Br, Cl or F, and n is preferably 1.

In another preferred embodiment, $R_3$ is H and n is preferably 1.

A more preferred embodiment of the compounds with the formula (II) comprises the following compounds:
7-Chloro-4-hydroxy-N'-octanoyl-2-oxo-2-hydroquinoline-3-carbohydrazide (14)
7-Chloro-N'-dodecanoyl-4-hydroxy-2-oxo-2-hydroquinoline-3-carbohydrazide (15)
6-Fluoro-N'-dodecanoyl-4-hydroxy-2-oxo-2-hydroquinoline-3-carbohydrazide (17)
4-Hydroxy-1(isoprenyl)-N'-octanoyl-2-oxo-1,2-dihydroquinoline-3-carbohydrazide (42)
N'-Dodecanoyl-4-hydroxy-1-(isoprenyl)-2-oxo-1,2-dihydroquinoline-3-carbohydrazide (43)
N'-Dodecanoyl-4-hydroxy-1-isobutyl-2-oxo-1,2-dihydroquinoline-3-carbohydrazide (44)
1-(Cyclopropylmethyl)-N'-dodecanoyl-4-hydroxy-2-oxo-1,2-dihydroquinoline-3-carbohydrazide (45)
1-Benzyl-N'-dodecanoyl-4-hydroxy-2-oxo-1,2-dihydroquinoline-3-carbohydrazide (46)
6-Bromo-N'-dodecanoyl-4-hydroxy-2-oxo-2-hydroquinoline-3-carbohydrazide (47)
6-Chloro-N'-dodecanoyl-4-hydroxy-2-oxo-2-hydroquinoline-3-carbohydrazide (48)
6-Bromo-4-hydroxy-1-methyl-N'-octanoyl-2-oxo-1,2-dihydroquinoline-3-carbohydrazide (49)
6-Bromo-N'-dodecanoyl-4-hydroxy-1-methyl-2-oxo-1,2-dihydroquinoline-3-carbohydrazide (50)
6-Bromo-1-ethyl-4-hydroxy-N'-octanoyl-2-oxo-1,2-dihydroquinoline-3-carbohydrazide (51)
6-Bromo-N'-dodecanoyl-1-ethyl-4-hydroxy-2-oxo-1,2-dihydroquinoline-3-carbohydrazide (52)
6-Chloro-4-hydroxy-1-methyl-N'-octanoyl-2-oxo-1,2-dihydroquinoline-3-carbohydrazide (53)
6-Chloro-N'-dodecanoyl-4-hydroxy-1-methyl-2-oxo-1,2-dihydroquinoline-3-carbohydrazide (54)
6-Chloro-1-ethyl-4-hydroxy-N'-octanoyl-2-oxo-1,2-dihydroquinoline-3-carbohydrazide (55)
6-Chloro-N'-dodecanoyl-1-ethyl-4-hydroxy-2-oxo-1,2-dihydroquinoline-3-carbohydrazide (56)
7-Chloro-4-hydroxy-1-methyl-N'-octanoyl-2-oxo-1,2-dihydroquinoline-3-carbohydrazide (57)
7-Chloro-N'-dodecanoyl-4-hydroxy-1-methyl-2-oxo-1,2-dihydroquinoline-3-carbohydrazide (58)
7-Chloro-1-ethyl-4-hydroxy-N'-octanoyl-2-oxo-1,2-dihydroquinoline-3-carbohydrazide (59)
7-Chloro-N'dodecanoyl-1-ethyl-4-hydroxy-2-oxo-1,2-dihydroquinoline-3-carbohydrazide (60)
1-Benzyl-7-chloro-4-hydroxy-N'-octanoyl-2-oxo-1,2-dihydroquinoline-3-carbohydrazide (61)
1-Benzyl-7-chloro-N'dodecanoyl-4-hydroxy-2-oxo-1,2-dihydroquinoline-3-carbohydrazide (62)
N',1-Dibenzyl-N'dodecanoyl-4-hydroxy-2-oxo-1,2-dihydroquinoline-3-carbohydrazide (63)

Another preferred embodiment relates to a compound selected from the following group:
N'-Dodecanoyl-1-ethyl-4-hydroxy-2-oxo-1,2-dihydroquinoline-3-carbohydrazide (6)
7-Chloro-N'-dodecanoyl-4-hydroxy-2-oxo-2-hydroguinoline-3-carbohydrazide (15)
6-Bromo-N'-dodecanoyl-4-hydroxy-2-oxo-2-hydroguinoline-3-carbohydrazide (47)
6-Chloro-N'-dodecanoyl-4-hydroxy-2-oxo-2-hydroquinoline-3-carbohydrazide (48)

6-Bromo-N'-dodecanoyl-1-ethyl-4-hydroxy-2-oxo-1,2-dihydroquinoline-3-carbohydrazide (52)
6-chloro-N'-dodecanoyl-1-ethyl-4-hydroxy-2-oxo-1,2-dihydroquinoline-3-carbohydrazide (56)
7-Chloro-N'-dodecanoyl-4-hydroxy-1-methyl-2-oxo-1,2-dihydroquinoline-3-carbohydrazide (58)
7-Chloro-N'dodecanoyl-1-ethyl-4-hydroxy-2-oxo-1,2-dihydroquinoline-3-carbohydrazide (60)

A third aspect of the present invention relates to the use of a compound with the formula (II), as described above, for the manufacturing of a medicament.

A fourth aspect of the present invention relates to a pharmaceutical composition that comprises a compound with the formula (II), as described above, jointly with a pharmaceutically adequate vehicle. In a preferred embodiment, this composition further comprises another known active principle, used for the treatment and/or prevention of any of the aforementioned diseases.

The compounds of the present invention represented by the formula (I) or the formula (II), and, more specifically, the specific compounds pertaining to this previously described general formula may include isomers, depending on the presence of multiple bonds (for example, Z, E), including optical isomers or enantiomers, depending on the presence of chiral centres. The individual isomers, enantiomers or diastereoisomers, and the mixtures thereof, fall within the scope of the present invention. The individual enantiomers or diastereoisomers, and the mixtures thereof, may be separated by means of conventional techniques.

The compounds of the invention may be in crystalline form as free compounds or as solvates, and both forms are intended to be included within the scope of the present invention. In this regard, the term "solvate", as used herein, includes both pharmaceutically acceptable solvates, i.e. solvates of the compound with the formula (I) that may be used in the preparation of a medicament, and pharmaceutically unacceptable solvates, which may be useful in the preparation of pharmaceutically acceptable solvates or salts. The nature of the pharmaceutically acceptable solvate is not critical, provided that it is pharmaceutically acceptable. In a particular embodiment, the solvate is a hydrate. The solvates may be obtained by conventional solvation methods that are well-known to persons skilled in the art.

The compounds with the formula (I) or the formula (II) designed for therapeutic use are prepared in solid form or aqueous suspension, in a pharmaceutically acceptable diluent. These preparations may be administered by any appropriate administration route, for which reason said preparation will be formulated in the adequate pharmaceutical form for the selected administration route. In a particular embodiment, administration of the compound with the formula (I) provided by this invention is performed by oral, topical, rectal or parenteral route (including subcutaneous, intraperitoneal, intradermal, intramuscular, intravenous route, etc.). A review of the different pharmaceutical forms for the administration of medicaments and the necessary excipients to obtain them may be found, for example, in "Tratado de Farmacia Galenica", C. Fauli i Trillo, 1993, Luzan 5, S. A. Ediciones, Madrid, or other habitual or similar ones in the Spanish Pharmacopeia and in the United States.

The compounds described in the present invention, their pharmaceutically acceptable salts and solvates, and the pharmaceutical compositions containing them may be used jointly with other, additional drugs, to provide combined therapy. Said additional drugs may be a part of the same pharmaceutical composition or, alternatively, may be provided in the form of a separate composition for simultaneous or non-simultaneous administration with the pharmaceutical composition comprising a compound with the formula (I) or the formula (II), or a pharmaceutically acceptable salt, stereoisomer or solvate thereof.

Except as otherwise specified, the compounds of the invention also include compounds that differ only in the presence of one or more isotope-enriched atoms. For example, compounds that have said structure, except for the substitution of a hydrogen atom by a deuterium or a tritium atom, or the substitution of a carbon atom by an enriched carbon in .sup.13C or .sup.14C, or a nitrogen atom enriched in .sup.15N, are included within the scope of this invention.

A final aspect of the present invention relates to a process for obtaining a compound with the formula (II), which comprises the following steps:

1) Reaction of a resin with a compound with the formula (III)

where R.sub.7 and R.sub.8 are identical or different C.sub.1-C.sub.5 groups alkyl.

2) Reaction of the product obtained in the preceding step with a product with the formula (IV):

where R.sub.3 is defined as above.

3) Reaction of the product obtained in the preceding step with a compound with the formula (V):

where R.sub.9 is a C.sub.1-C.sub.5 alkyl group.

4) Cyclisation of the product obtained in the preceding step.

5) Reaction of the product obtained in the preceding step with a compound with the formula (VI):

where R.sub.2 is defined as above.

In a preferred embodiment of the process of the invention, R.sub.7 and R.sub.8 are independently a C.sub.1-C.sub.3alkyl group and, more preferably, a methyl group. In a preferred embodiment of the process of the invention, R.sub.9 is a C.sub.1-C.sub.3, alkyl group and, more preferably, it is an ethyl group.

Throughout the description and the claims, the word "comprises" and the variants thereof are not intended to exclude other technical characteristics, additives, components or steps. For persons skilled in the art, other objects, advantages and characteristics of the invention will arise partly from the description and partly from the practise of the invention. The following examples and figures are provided for illustrative purposes, and are not intended to limit the scope of this invention.

EXAMPLES

Below, we will illustrate the invention by means of assays performed by the inventors, which demonstrate the specificity and effectiveness of the compounds of the invention.

Compounds 1-17 were synthesised according to the synthetic pathways shown in diagrams 1 and 2.

General Synthesis Process for Compounds 1 and 2

Diagram 1

-continued

R$_1$ = Me  Comp. 1
R$_1$ = Me  Comp. 1
R$_1$ = Et  Comp. 2
R$_1$ = Et  Comp. 2

R$_2$ = (CH$_2$)$_6$CH$_3$  Comp. 3
R$_2$ = (CH$_2$)$_{10}$CH$_3$  Comp. 4
R$_2$ = (CH$_2$)$_{10}$CH$_3$  Comp. 6

The corresponding anhydride (1 equiv) is dissolved in 40 ml of DMF, and the sodium hydride (1.2 equiv) and diethyl malonate (1.2 equiv) are added. Subsequently, it is heated to 85.degree. C. for 6 h. After this time has elapsed, the mixture is allowed to cool and acidified with a 1 M HCl solution. When it reaches an acid medium, it precipitates a white solid which, after being filtered, is the pure final compound.

Ethyl 4-Hydroxy-1-methyl-2-oxo-1,2-dihydroquinoline-3-carboxylate (1). Yield 56%. .sup.1H NMR (300 MHz, CDCl.sub.3) .delta. 8.12 (d, J=8.0 Hz, 1H), 7.64 (t, J=7.9 Hz, 1H), 7.36-7.11 (m, 3H), 4.48 (q, J=7.1 Hz, 2H), 3.61 (s, 3H), 1.99 (sa, 1H), 1.46 (t, J=7.1 Hz, 3H). .sup.13C NMR (75 MHz, CDCl.sub.3) .delta. 172.8, 171.8, 159.7, 141.4, 134.5, 125.9, 122.0, 115.0, 114.3, 98.1, 62.4, 29.35, 14.44. M.p.=95.degree. C.-96.degree. C. HPLC: Purity>99%. MS (ES): m/z=248, 201, 133. Elementary Analysis (C.sub.13H.sub.13NO.sub.4) Calculated: C, 63.15%; H, 5.30%; N, 5.67%. Found: C, 63.31%; H, 5.08%; N, 5.77%.

Ethyl 1-Ethyl-4-hydroxy-2-oxo-1,2-dihydroquinoline-3-carboxylate (2). Yield 56%. .sup.1H NMR (300 MHz, CDCl.sub.3) .delta. 14.22 (s, 1H), 8.20 (dd, J=8.1, 1.5 Hz, 1H), 7.68 (ddd, J=8.7, 7.2, 1.6 Hz, 1H), 7.39-7.16 (m, 2H), 4.51 (q, J=7.1 Hz, 2H), 4.31 (q, J=7.1 Hz, 2H), 1.49 (t, J=7.1 Hz, 3H), 1.34 (t, J=7.1 Hz, 3H). .sup.13C NMR (75 MHz, CDCl.sub.3) .delta. 172.5, 171.4, 159.0, 140.1, 134.1, 125.7, 121.5, 114.9, 113.8, 97.7, 62.1, 37.0, 14.0, 12.5. M.p.=68.degree. C.-69.degree. C. HPLC: Purity 97%. MS (ES): m/z=263, 217, 187. Elementary analysis (C.sub.14H.sub.15NO.sub.4) Calculated: C, 64.36%; H, 5.79%; N, 5.36%. Found: C, 64.72%; H, 5.63%; N, 5.05%.

General Synthesis Process for Compounds 3-6

1 equivalent of 1 or 2, as specified in each case, the corresponding hydrazide (1 equiv) and 0.2 ml of DMF are placed in a flask, and heated to 160.degree. C. for 3 min. It is allowed to cool, MeOH is carefully added, and a white solid precipitates, which is filtered and purified by means of MeOH washings.

4-Hydroxy-1-methyl-N'-octanoyl-2-oxo-1,2-dihydroquinoline-3-carbohydrazide (3). Reagents: Compound 1 and octanoyl hydrazide.

Yield 99%. .sup.1H NMR (300 MHz, CDCl.sub.3) .delta. 15.49 (s, 1H), 12.46 (d, J=5.6 Hz, 1H), 8.28 (d, J=5.7 Hz, 1H), 8.18 (dd, J=8.1, 1.5 Hz, 1H), 7.71 (t, J=7.9 Hz, 1H), 7.44-7.27 (m, 2H), 3.69 (s, 3H), 2.44-2.20 (t, J=7.6 Hz, 2H), 1.90-1.56 (m, 2H), 1.45-1.18 (m, 8H), 0.88 (t, J=6.8 Hz, 3H). .sup.13C NMR (75 MHz, CDCl.sub.3) .delta. 172.4, 171.4, 166.9, 162.4, 140.2, 134.8, 126.2, 129.9, 115.8, 115.1, 96.1, 34.4, 31.8, 31.3, 29.6, 29.4, 25.4, 22.7, 14.1. M.p.=157.degree. C.-158.degree. C. HPLC: Purity>99%. MS (ES): m/z=360, 234. Elementary Analysis (C.sub.19H.

sub.25N.sub.3O.sub.4) Calculated: C, 63.49%; H, 7.01%; N, 11.69%. Found: C, 63.76%; H, 6.94%; N, 11.65%.

N'-Dodecanoyl-4-hydroxy-1-methyl-2-oxo-1,2-dihydroquinoline-3-carbohydrazide (4). Reagents: Compound 1 and dodecanoyl hydrazide.

Yield 93%. $^1$H NMR (300 MHz, DMSO) .delta. 15.50 (s, 1H), 12.47 (d, J=5.6 Hz, 1H), 8.20 (d, J=8.1 Hz, 1H), 8.16 (d, J=5.9 Hz, 1H), 7.72 (t, J=8.0 Hz, 1H), 7.42-7.29 (m, 1H), 3.70 (s, 3H), 2.32 (t, J=7.6 Hz, 2H), 1.77-1.66 (m, 2H), 1.26 (s, 16H), 0.88 (t, J=6.6 Hz, 3H). $^{13}$C NMR (75 MHz, CDCl.sub.3) .delta. 171.1, 169.0, 166.6, 161.9, 140.1, 134.1, 125.4, 122.5, 115.6, 114.3, 96.2, 34.4, 31.8, 29.5, 29.4, 29.3, 29.1, 25.4, 22.6, 14.0. M.p.=219.degree. C.-220.degree. C. HPLC: Purity>99%. MS (ES): m/z=416, 234. Elementary Analysis (C.sub.23H.sub.33N.sub.3O.sub.4) Calculated: C, 66.48%; H, 8.00%; N, 10.11%. Found: C, 64.76%; H, 7.79%; N, 10.27%.

N'-Dodecanoyl-1-ethyl-4-hydroxy-2-oxo-1,2-dihydroquinoline-3-carbohydrazide (6). Reagents: Compound 2 and dodecanoyl hydrazide.

Yield 91%. $^1$H NMR (300 MHz, DMSO) .delta. 16.22 (s, 1H), 12.05 (d, J=3.7 Hz, 1H), 10.80 (d, J=3.7 Hz, 1H), 8.09 (d, J=8.0 Hz, 1H), 7.82 (t, J=7.1 Hz, 1H), 7.68 (d, J=8.6 Hz, 1H), 7.38 (t, J=7.4 Hz, 1H), 4.31 (d, J=6.7 Hz, 2H), 2.24 (m, 2H), 1.55 (m, 2H), 1.23 (m, 19H), 0.84 (m, 3H). $^{13}$C NMR (75 MHz, DMSO) .delta. 171.3, 170.3, 167.9, 161.5, 139.5, 135.2, 125.3, 123.2, 115.8, 96.4, 37.6, 33.7, 31.9, 29.6, 29.5, 29.3, 29.2, 25.6, 22.7, 14.5, 13.3. M.p.=133.degree. C.-134.degree. C. HPLC: Purity>99%. MS (ES): m/z=430, 248. Elementary Analysis (C.sub.24H.sub.35N.sub.3O.sub.4) Calculated: C, 67.11%; H, 8.21%; N, 9.78%. Found: C, 67.40%; H, 8.31%; N, 9.88%.

General Synthesis Process for Compounds 12-17

Diagram 2

The Merrifield resin (7) (1 equiv) is added on dry dimethylacetamide and the mixture is bubbled with argon. 4-hydroxy-2,6-dimethoxybenzaldehyde (2.13 equiv) dissolved in dimethylacetamide and cesium carbonate (2.56 equiv) are added. The vial is hermetically sealed and allowed to react at 85.degree. C. for 36 h. After conveniently washing resin 8, dry dichloromethane, the corresponding methyl benzoate derivative (3 equiv) and sodium triacetoxyborohydride (3 equiv) are added. The mixture is left under stirring at room temperature for 16 h. Following the corresponding washings, dry dichloromethane, ethyl monomalonate (3 equiv), phosphoryl oxychloride (3 equiv) and pyridine (6 equiv) are added to resin 9, and it is left under stirring at room temperature for 2 h. After the corresponding washings, dry THF and a 0.5 M solution of KHMDS in toluene (10 equiv) are added to resin 10, and it is allowed to react for 12 h at room temperature. Following the corresponding washings, resin 11 is unanchored using a TFACH.sub.2Cl.sub.2 solution (50:50) under stirring for 1 h at room temperature. The mixture is filtered and the filtrate is washed with water. The organic phase is dried with MgSO.sub.4 and the solvent is evaporated at reduced pressure. The product obtained is made to react with the corresponding hydrazide (1 equiv) in DMF and heated to 160.degree. C. for 3 min. It is allowed to cool, MeOH is added, and a white solid precipitates, which is filtered and subsequently purified by means of MeOH washings.

N'-Dodecanoyl-4-hydroxy-2-oxo-2-hydroquinoline-3-carbohydrazide (13). Reagents: methyl anthranilate and dodecanoyl hydrazide.

Yield 98%. $^1$H NMR (300 MHz, DMSO) δ. 16.11 (s, 1H), 11.98 (s, 1H), 11.92 (s, 1H), 10.63 (s, 1H), 7.98 (d, J=8.1 Hz, 1H), 7.71 (t, J=7.7 Hz, 1H), 7.39 (d, J=8.3 Hz, 1H), 7.31 (t, J=7.6 Hz, 1H), 2.23 (t, J=7.2 Hz, 2H), 1.57 (d, J=6.6 Hz, 2H), 1.25 (s, 16H), 0.85 (t, J=6.2 Hz, 3H). $^{13}$C NMR (75 MHz, DMSO) δ. 172.2, 170.0, 167.8, 162.3, 139.1, 134.5, 124.3, 122.9, 116.3, 114.5, 99.4, 33.2, 31.6, 31.0, 29.3, 29.0, 28.8, 25.3, 22.4, 14.3. M.p.=256.degree. C.-257.degree. C. HPLC: Purity>99%. MS (ES): m/z=402, 220. Elementary Analysis ($C_{22}H_{31}N_3O_4$) Calculated: C, 65.81%; H, 7.78%; N, 10.47%. Found: C, 66.02%; H, 7.83%; N, 10.74%.

7-Chloro-4-hydroxy-N'-octanoyl-2-oxo-2-hydroquinoline-3-carbohydrazide (14). Reagents: methyl 2-amino-4-chlorobenzoate and octanoyl hydrazide.

Yield 86%. $^1$H NMR (300 MHz, DMSO) δ. 16.11 (sa, 1H), 12.09 (s, 1H), 11.79 (s, 1H), 10.71 (d, J=3.1 Hz, 1H), 7.94 (d, J=5.0 Hz, 1H), 7.48-7.16 (m, 2H), 2.87 (s, 2H), 2.71 (s, 2H), 2.49 (s, 2H), 2.21 (t, J=7.3 Hz, 2H), 1.61-1.42 (m, 2H), 1.25 (s, 8H), 0.85 (t, J=6.6 Hz, 3H). M.p.=290.degree. C.-291.degree. C. HPLC: Purity 95%. MS (ES): m/z=380, 254, 222. Elementary Analysis ($C_{18}H_{22}ClN_3O_4$) Calculated: C, 56.92%; H, 5.84%; N, 11.06%. Found: C, 56.84%; H, 5.73%; N, 11.00%.

7-Chloro-N'-dodecanoyl-4-hydroxy-2-oxo-2-hydroquinoline-3-carbohydrazide (15). Reagents: methyl 2-amino-4-chlorobenzoate and dodecanoyl hydrazide.

Yield last reaction 92%. $^1$H NMR (300 MHz, DMSO) δ. 16.21 (s, 1H), 12.10 (s, 1H), 11.80 (s, 1H), 10.71 (s, 1H), 7.98 (d, J=8.6 Hz, 1H), 7.42 (d, J=1.8 Hz, 1H), 7.31 (dd, J=8.7, 2.0 Hz, 1H), 2.87 (s, 2H), 2.71 (s, 2H), 2.20 (t, J=7.4 Hz, 2H), 1.53 (s, 2H), 1.23 (s, 12H), 0.82 (d, J=6.7 Hz, 3H). M.p.=291-292.degree. C. HPLC: Purity 97%. MS (ES): m/z=436, 254, 222. Elementary Analysis ($C_{22}H_{30}ClN_3O_4$) Calculated: C, 60.42%; H, 6.94%; N, 9.64%. Found: C, 60.42%; H, 6.71%; N, 9.58%.

6-Fluoro-N'-dodecanoyl-4-hydroxy-2-oxo-2-hydroquinoline-3-carbohydrazide (17). Reagents: methyl 2-amino-5-fluorobenzoate and dodecanoyl hydrazide.

Yield 93%. $^1$H NMR (400 MHz, DMSO) δ. 11.86 (s, 1H), 10.42 (s, 1H), 7.64 (d, J=6.9 Hz, 1H), 7.56 (td, J=8.7, 2.9 Hz, 1H), 7.42 (dd, J=9.2, 4.5 Hz, 1H), 2.47 (m, 2H), 2.21 (t, J=7.3 Hz, 2H), 1.66-1.42 (m, 2H), 1.24 (s, 14H), 0.83 (t, J=6.9 Hz, 3H). M.p.=178.degree. C.-179.degree. C. HPLC: Purity 95%. MS (ES): m/z=420, 238, 206. Elementary Analysis ($C_{22}H_{30}FN_3O_4$) Calculated: C, 62.99%; H, 7.21%; N, 10.02%. Found: C, 63.20%; H, 7.42%; N, 9.87%.

General Synthesis Process for Compounds 18-28

The corresponding isatoic anhydride (1 equiv) is dissolved in 15 ml of anhydrous DMF and, subsequently, sodium hydride (1.5 equiv) is added slowly at 0.degree. C. After 30 minutes, the corresponding halogenated derivative is added (1.5-3 equiv) and the reaction is left under stirring at room temperature overnight. Subsequently, dichloromethane (15 ml) and water (15 ml) are added. The organic phase is separated, and the aqueous phase is once again extracted with dichloromethane (15 ml). The organic phases are brought together and washed with a saturated NaCl solution (15 ml). The organic phase is dried on anhydrous magnesium sulfate and filtered, and the solvent is evaporated under vacuum. The resulting solid is recrystallised in dichloromethane/hexane, to produce the desired final product.

Diagram 3

| $R_3$ = H    | $R_1$ = isoprenyl           | Comp 18 |
| $R_3$ = H    | $R_1$ = isobutyl            | Comp 19 |
| $R_3$ = H    | $R_1$ = $CH_2$-cyclopropyl  | Comp 20 |
| $R_3$ = H    | $R_1$ = $CH_2$—Ph           | Comp 21 |
| $R_3$ = 6-Br | $R_1$ = Me                  | Comp 22 |
| $R_3$ = 6-Br | $R_1$ = Et                  | Comp 23 |
| $R_3$ = 6-Cl | $R_1$ = Me                  | Comp 24 |
| $R_3$ = 6-Cl | $R_1$ = Et                  | Comp 25 |
| $R_3$ = 7-Cl | $R_1$ = Me                  | Comp 26 |
| $R_3$ = 7-Cl | $R_1$ = Et                  | Comp 27 |
| $R_3$ = 7-Cl | $R_1$ = $CH_2$—Ph           | Comp 28 |

N-isoprenyl isatoic anhydride (18)

Reagents: Isatoic anhydride (6.13 mmols, 1 g); Sodium hydride (9.2 mmols, 0.23 g); Isoprenyl bromide (12 mmols, 1.9 g). Yield: 0.95 g (67%), white solid, m.p.=119.degree. C.-120.degree. C.

$^1$H NMR (300 MHz, DMSO-$d_6$) δ (ppm): 8.01 (d, J=1.6, 7.8 Hz, 1H), 7.85 (t, J=1.6, 7.3, 8.8 Hz, 1H), 7.32-7.26 (m, 2H), 5.19 (t, J=1.4, 6.4 Hz, 1H), 4.64 (d, J=6.2 Hz, 2H), 1.81 (s, J=1.4 Hz, 3H), 1.70 (s, J=1.4 Hz, 3H); $^{13}$C NMR (75 MHz, DMSO-$d_6$) δ (ppm): 159.9, 147.6, 141.3, 137.1, 136.4, 129.6, 123.6, 118.2, 111.9, 42.7, 25.4, 18.1. HPLC: Purity>99%, r.t.=8.9 min. ESI MS (m/z): 232 [M+H]$^+$.

N-isobutyl isatoic anhydride (19)

Reagents: Isatoic anhydride (6.13 mmols, 1 g); Sodium hydride (9.2 mmols, 0.22 g); isobutyl iodide (18 mmols, 3.4 g). Yield: 0.6 g (46%), white solid, m.p.=85.degree. C.-86.degree. C.

$^1$H NMR (300 MHz, DMSO-$d_6$) δ (ppm): 8.10 (dd, J=1.7, 7.9 Hz, 1H), 7.68 (ddd, J=1.6, 7.3, 8.4 Hz, 1H), 7.25-7.18 (m, 1H), 7.10 (d, J=8.5 Hz, 1H) 3.93 (d, J=7.6 Hz, 2H), 2.25-2.10 (m, 1H), 1.03 (d, J=6.7 Hz, 6H); $^{13}$C NMR (75 MHz, CDCl$_3$) δ (ppm): 162.4, 158.7, 148.3, 141.8, 137.2, 131.1, 124.0, 114.4, 112.0, 51.7, 26.9, 20.1, 19.9. HPLC: Purity>99%, r.t.=8.6 min. ESI MS (m/z): 220 [M+H]$^+$.

N-(cyclopropylmethyl)isatoic anhydride (20)

Reagents: Isatoic anhydride (4.9 mmols, 0.8 g); Sodium hydride (5.9 mmols, 0.14 g); Cyclopropylmethyl bromide (5.9 mmols, 0.8 g). Yield: 0.53 g (50%), light brown solid, m.p.=122.degree. C.-123.degree. C.

$^1$H NMR (300 MHz, DMSO-$d_6$) δ (ppm): 8.11 (dd, J=1.6, 7.7 Hz, 1H), 7.75-7.67 (m, 1H), 7.27-7.20 (m, 2H), 3.95 (d, J=7.0 Hz, 2H), 1.25-1.10 (m, 1H), 0.54-

0.40 (m, 4H); .sup.13C NMR (75 MHz, CDCl.sub.3) .delta. (ppm): 158.7, 148.4, 141.7, 137.3, 131.0, 124.0, 114.3, 111.9, 49.2, 9.3, 4.1. HPLC: Purity>97%, r.t.=8.2 min. ESI MS (m/z): 218 [M+H].sup.+.

N-Benzyl Isatoic Anhydride (21)

Reagents: Isatoic anhydride (6.13 mmols, 1 g); Sodium hydride (9.2 mmols, 0.22 g); Benzyl bromide (12.3 mmols, 1.4 g). Yield: 0.2 g (15%), white solid, m.p.=139.degree. C.-140.degree. C.

.sup.1H NMR (300 MHz, CDCl.sub.3) .delta. (ppm): 8.10 (dd, J=1.6, 7.8 Hz, 1H), 7.56 (td, J=1.6, 7.3, 8.7 Hz, 1H), 7.35-7.10 (m, 6H), 7.05 (dd, J=8.5 Hz, 1H), 5.24 (s, 2H); .sup.13C NMR (75 MHz, CDCl.sub.3) .delta. (ppm): 157.3, 147.4, 140.3, 136.2, 133.4, 129.8, 128.1, 127.1, 125.7, 123.1, 113.7, 110.8, 47.5. HPLC: Purity>99%, r.t.=8.7 min. ESI MS (m/z): 254 [M+H].sup.+.

6-bromo-N-methyl isatoic anhydride (22)

Reagents: 5-bromo isatoic anhydride (4.13 mmols, 1 g); Sodium hydride (6.2 mmols, 0.15 g); Methyl iodide (6.2 mmols, 0.9 g). Yield: 0.69 g (66%), white solid, m.p.=201.degree. C.-202.degree. C.

.sup.1H NMR (300 MHz, CDCl.sub.3) .delta. (ppm): 8.06 (d, J=2.5 Hz, 1H), 7.64 (dd, J=2.5, 9.0 Hz, 1H), 7.08 (d, J=9.0 Hz, 1H), 2.92 (s, 3H); .sup.-C NMR (75 MHz, CDCl.sub.3) .delta. (ppm): 157.2, 147.4, 141.0, 140.0, 133.0, 116.9, 115.6, 113.2, 32.0. HPLC: Purity>98%, r.t.=7.7 min. ESI MS (m/z): 256 [M+H].sup.+.

6-bromo-N-ethyl isatoic anhydride (23)

Reagents: 5-bromo isatoic anhydride (8.26 mmols, 2 g); Sodium hydride (12.5 mmols, 0.3 g); Ethyl iodide (12.5 mmols, 1.9 g). Yield: 1.4 g (63%), white solid, m.p.=177.degree. C.-178.degree. C.

.sup.1H NMR (300 MHz, CDCl.sub.3) .delta. (ppm): 8.21 (d, J=2.4 Hz, 1H), 7.78 (dd, J=2.4, 8.9 Hz, 1H), 7.02 (d, J=8.9 Hz, 1H), 4.05 (c, J=7.2 Hz, 2H), 1.31 (t, J=7.2 Hz, 3H); .sup.-C NMR (75 MHz, CDCl.sub.3) .delta. (ppm): 157.3, 146.9, 140.0, 139.0, 133.2, 116.6, 115.5, 113.4, 40.3, 12.0. HPLC: Purity>97%, r.t.=8.4 min. ESI MS (m/z): 270 [M+H].sup.+.

6-chloro-N-methyl isatoic anhydride (24)

Reagents: 5-chloro isatoic anhydride (3.97 mmols, 0.78 g); Sodium hydride (5.95 mmols, 0.14 g); Methyl iodide (11.4 mmols, 1.6 g). Yield: 0.5 g (60%), white solid, m.p.=203.degree. C.-204.degree. C.

.sup.1H NMR (300 MHz, CDCl.sub.3) .delta. (ppm): 8.05 (d, J=2.5 Hz, 1H), 7.66 (dd, J=2.5, 8.9 Hz, 1H), 7.09 (d, J=8.9 Hz, 1H), 3.52 (s, 3H); .sup.-C NMR (75 MHz, CDCl.sub.3) .delta. (ppm): 156.3, 146.4, 139.5, 136.2, 129.0, 114.4, 111.9. HPLC: Purity>98%, r.t.=7.3 min.

6-chloro-N-ethyl isatoic anhydride (25)

Reagents: 5-chloro isatoic anhydride (2.53 mmols, 0.5 g); Sodium hydride (3.8 mmols, 0.09 g); Ethyl iodide (3.8 mmols, 0.6 g). Yield: 0.4 g (70%), white solid, m.p.=150.degree. C.-151.degree. C.

.sup.1H NMR (300 MHz, CDCl.sub.3) .delta. (ppm): 8.07 (d, J=2.5 Hz, 1H), 7.64 (dd, J=2.5, 8.9 Hz, 1H), 7.08 (d, J=8.9 Hz, 1H), 4.06 (c, J=7.2 Hz, 2H), 1.31 (t, J=7.2 Hz, 3H); .sup.-C NMR (75 MHz, CDCl.sub.3) .delta. (ppm): 171.5, 169.5, 164.1, 157.8, 137.8, 133.3, 126.4, 124.2, 115.1, 114.5, 97.5, 36.4, 13.2. HPLC: Purity>99%, r.t.=8.3 min. ESI MS (m/z): 226 [M+H].sup.+.

7-chloro-N-methyl isatoic anhydride (26)

Reagents: 4-chloro isatoic anhydride (4.55 mmols, 0.9 g); Sodium hydride (5.46 mmols, 0.9 g); Methyl iodide (13.7 mmols, 1.9 g). Yield: 0.4 g (42%), yellow solid, m.p.=215.degree. C.-216. degree. C.

.sup.1H NMR (300 MHz, DMSO-d.sub.6) .delta. (ppm): 7.99 (d, J=8.4 Hz, 1H), 7.59 (d, J=1.8 Hz, 1H), 7.39 (dd, J=1.8, 8.4 Hz, 1H), 3.46 (s, 3H); .sup.-C NMR (75 MHz, DMSO-d.sub.6) .delta. (ppm): 158.6, 147.9, 143.9, 142.3, 131.4, 124.1, 115.4, 111.1, 32.4. HPLC: Purity>96%, r.t.=7.3 min. ESI MS (m/z): 212 [M+H].sup.+.

7-chloro-N-ethyl isatoic anhydride (27)

Reagents: 4-chloro isatoic anhydride (4.55 mmols, 0.9 g); Sodium hydride (5 mmols, 0.12 g); Ethyl iodide (8.3 mmols, 1.3 g). Yield: 0.65 g (63%), white solid, m.p.=156.degree. C.-157.degree. C.

.sup.1H NMR (300 MHz, DMSO-d.sub.6) .delta. (ppm): 8.00 (d, J=8.4 Hz, 1H), 7.64 (d, J=1.7 Hz, 1H), 7.37 (dd, J=1.7, 8.4 Hz, 1H), 4.06 (c, J=7.0 Hz, 2H), 1.20 (t, J=7.0 Hz, 3H); .sup.-C NMR (75 MHz, DMSO-d.sub.6) .delta. (ppm): 158.8, 147.6, 142.8, 142.5, 131.8, 124.1, 114.9, 111.4, 40.2, 12.3. HPLC: Purity>97%, r.t.=8.1 min. ESI MS (m/z): 226 [M+H].sup.+.

7-chloro-N-benzyl isatoic anhydride (28)

Reagents: 4-chloro isatoic anhydride (5 mmols, 1.0 g); Sodium hydride (7.83 mmols, 0.19 g); Benzyl bromide (10.1 mmols, 1.7 g). Yield: 0.9 g (38%), white solid, m.p.= 207.degree. C.-208.degree. C.

.sup.1H NMR (300 MHz, DMSO-d.sub.6) .delta. (ppm): 8.03 (d, J=8.3 Hz, 1H), 7.42 (m, 2H), 7.37 (m, 1H), 7.35 (m, 3H), 7.29 (m, 1H), 5.31 (s, 2H); .sup.-C NMR (75 MHz, DMSO-d.sub.6) .delta. (ppm): 158.2, 148.1, 142.5, 141.5, 135.0, 131.2, 128.7, 127.4, 126.6, 123.8, 114.9, 111.3, 47.6. HPLC: Purity>99%, r.t.=9.4 min. ESI MS (m/z): 288 [M+H].sup.+.

General Synthesis Process for Compounds 29-41

Diethyl malonate is added drop by drop on a solution of sodium hydride in anhydrous DMF (15 ml) under a nitrogen atmosphere. The mixture is left under stirring for 30 minutes at room temperature. Subsequently, the reaction is added to a flask containing the corresponding isatoic anhydride derivative dissolved in anhydrous DMF (15 ml) under a Nitrogen atmosphere. The mixture is heated to 50.degree. C. for 5 hours. Dichloromethane (30 ml), water (50 ml) and an HCl solution (1 N) are added to the mixture up to pH=5. The organic phase is separated, and the aqueous phase is once again extracted with dichloromethane (30 ml). The organic phases are brought together and washed with a saturated NaCl solution (30 ml). The organic phase is dried on anhydrous magnesium sulfate and filtered, and the solvent is evaporated under vacuum. The resulting solid is recrystallised in dichloromethane/hexane, to produce the desired final product.

Diagram 4

| | | |
|---|---|---|
| $R_3$ = H | $R_1$ = isoprenilo | Comp 29 |
| $R_3$ = H | $R_1$ = isobutilo | Comp 30 |
| $R_3$ = H | $R_1$ = $CH_2$-ciclopropilo | Comp 31 |
| $R_3$ = H | $R_1$ = $CH_2$—Ph | Comp 32 |
| $R_3$ = 6-Br | $R_1$ = H | Comp 33 |
| $R_3$ = 6-Cl | $R_1$ = H | Comp 34 |
| $R_3$ = 6-Br | $R_1$ = Me | Comp 35 |
| $R_3$ = 6-Br | $R_1$ = Et | Comp 36 |
| $R_3$ = 6-Cl | $R_1$ = Me | Comp 37 |
| $R_3$ = 6-Cl | $R_1$ = Et | Comp 38 |
| $R_3$ = 7-Cl | $R_1$ = Me | Comp 39 |
| $R_3$ = 7-Cl | $R_1$ = Et | Comp 40 |
| $R_3$ = 7-Cl | $R_1$ = $CH_2$—Ph | Comp 41 |

Ethyl 4-hydroxy-1-(isoprenyl)-2-oxo-1,2-dihydroquinoline-3-carboxylate (29)

Reagents: Comp 18 (1.3 mmols, 0.3 g); Sodium hydride (1.3 mmols, 0.065 g); Diethyl malonate (6.5 mmols, 1.0 g). Yield: 0.08 g (21%), white solid, m.p.=123.degree. C.-124.degree. C.

$^1$H NMR (300 MHz, DMSO-d$_6$) .delta. (ppm): 14.2 (s, 1H), 8.18 (dd, J=1.6, 8.3 Hz, 1H), 7.65 (td, J=1.6, 7.1, 7.9 Hz, 1H), 7.24 (m, 2H), 5.10 (m, 1H), 4.88 (d, J=6.0 Hz, 2H), 4.51 (c, J=7.1 Hz, 2H), 1.80 (s, 3H), 1.63 (s, 3H), 1.41 (t, J=7.1 Hz, 3H); $^{13}$C NMR (75 MHz, CDCl$_3$) .delta. (ppm): 172.9, 171.8, 159.5, 140.9, 135.8, 134.3, 125.9, 121.8, 119.7, 115.2, 114.7, 98.0, 62.5, 40.9, 25.7, 18.5, 14.4. HPLC: Purity>96%, r.t.=10.2 min. ESI MS (m/z): 302 [M+H]$^+$.

Ethyl 4-hydroxy-1-isobutyl-2-oxo-1,2-dihydroquinoline-3-carboxylate (30)

Reagents: Comp 19 (1.36 mmols, 0.3 g); Sodium hydride (5.75 mmols, 0.138 g); Diethyl malonate (6.84 mmols, 1.1 g). Yield: 0.15 g (38%), yellow oil.

$^1$H NMR (300 MHz, DMSO-d$_6$) .delta. (ppm): 13.02 (s, 1H), 8.06 (dd, J=1.55, 8.3 Hz, 1H), 7.72 (ddd, J=1.60, 7.0, 8.7 Hz, 1H), 7.55 (d, J=8.6 Hz, 1H), 7.29 (ddd, J=0.86, 7.0, 7.9 Hz, 1H), 4.33 (c, J=8.6 Hz, 2H), 4.07 (d, J=7.4 Hz, 2H), 2.10 (sept, J=7.0 Hz, 1H), 1.31 (t, J=7.4 Hz, 3H), 0.89 (d, J=7.4 Hz, 6H); $^{13}$C NMR (75 MHz, DMSO-d$_6$) .delta. (ppm): 169.2, 165.5, 158.9, 140.0, 133.6, 124.6, 121.7, 115.3, 114.5, 101.0, 61.4, 47.5, 26.6, 19.8, 13.9. HPLC: Purity>95%, r.t.=10.0 min. ESI MS (m/z): 290 [M+H]$^+$.

Ethyl 1-(cyclopropylmethyl)-4-hydroxy-2-oxo-1,2-dihydroquinoline-3-carboxylate (31)

Reagents: Comp 20 (1.38 mmols, 0.3 g); Sodium hydride (2.91 mmols, 0.07 g); Diethyl malonate (6.91 mmols, 1.1 g).

The reaction product (white solid) is not purified and is used for the following reaction step. $^1$H NMR (300 MHz, DMSO-d$_6$) .delta. (ppm): 14.2 (s, 1H), 8.13 (dt, J=1.25, 8.1 Hz, 1H), 7.61 (td, J=1.59, 7.27, 7.97 Hz, 1H), 7.37 (d, J=8.63 Hz, 1H), 7.18 (m, 1H), 4.44 (c, J=7.12 Hz, 2H), 4.12 (d, J=6.67 Hz, 2H), 1.41 (t, J=7.12 Hz, 3H), 1.25-1.10 (m, 1H), 0.55-0.38 (m, 4H); HPLC: Purity>86%, r.t.=9.7 min. ESI MS (m/z): 288 [M+H]$^+$.

Ethyl 1-benzyl-4-hydroxy-2-oxo-1,2-dihydroquinoline-3-carboxylate (32)

Reagents: Comp 21 (3.4 mmols, 0.85 g); Sodium hydride (7.37 mmols, 0.18 g); Diethyl malonate (16.8 mmols, 2.7 g). Yield: 0.1 g (9%), white solid, m.p.=117.degree. C.-118.degree. C.

$^1$H NMR (300 MHz, CDCl$_3$) .delta. (ppm): 14.29 (s, 1H), 8.13 (dd, J=1.5, 8.0 Hz, 1H), 7.48-7.43 (m, 1H), 7.23-7.18 (m, 2H), 7.15-7.11 (m, 5H), 5.44 (s, 2H), 4.45 (c, J=7.1 Hz, 2H), 1.42 (t, J=7.1 Hz, 3H); $^{13}$C NMR (75 MHz, CDCl$_3$) .delta. (ppm): 171.7, 171.0, 158.7, 139.8, 135.4, 133.3, 127.7, 126.2, 125.4, 124.7, 121.0, 113.9, 96.8, 61.4, 44.6, 13.21. HPLC: Purity>99%, r.t.=9.9 min. ESI MS (m/z): 324 [M+H]$^+$.

Ethyl 6-bromo-4-hydroxy-2-oxo-1,2-dihydroquinoline-3-carboxylate (33)

Reagents: 5-bromo isatoic anhydride (4.1 mmols, 1.0 g); Sodium hydride (8.3 mmols, 0.2 g); Diethyl malonate (20.8 mmols, 3.3 g).

The final product is not isolated and is used for the following reaction step.

Ethyl 6-chloro-4-hydroxy-2-oxo-1,2-dihydroquinoline-3-carboxylate (34)

Reagents: 5-chloro isatoic anhydride (5.0 mmols, 1.0 g); Sodium hydride (10.4 mmols, 0.25 g); Diethyl malonate (25 mmols, 4.0 g).

The final product is not isolated and is used for the following reaction step.

Ethyl 6-bromo-4-hydroxy-1-methyl-2-oxo-1,2-dihydroquinoline-3-carboxylate (35)

Reagents: Comp 22 (2.3 mmols, 0.6 g); Sodium hydride (4.8 mmols, 0.12 g); Diethyl malonate (11.5 mmols, 1.8 g). Yield: 0.3 g (40%), white solid, m.p.=139.degree. C.-140.degree. C.

$^{1}$H NMR (300 MHz, CDCl$_3$) .delta. (ppm): 14.14 (s, 1H), 8.28 (d, J=2.4 Hz, 1H), 7.74 (dd, J=2.4, 9.0 Hz, 1H), 7.18 (d, J=9.0 Hz, 1H), 4.50 (c, J=7.1 Hz, 2H), 3.62 (s, 3H), 1.48 (t, J=7.1 Hz, 3H); .sup.-C NMR (75 MHz, CDCl$_3$) .delta. (ppm): 172.5, 170.6, 159.3, 140.3, 137.2, 128.2, 116.5, 116.0, 115.0, 98.7, 62.7, 29.4, 14.3. HPLC: Purity>96%, r.t.=9.6 min. ESI MS (m/z): 328 [M+H].sup.+.

Ethyl 6-bromo-1-ethyl-4-hydroxy-2-oxo-1,2-dihydroquinoline-3-carboxylate (36)

Reagents: Comp 23 (1.8 mmols, 0.5 g); Sodium hydride (3.7 mmols, 0.09 g); Diethyl malonate (4.25 mmols, 1.5 g). Yield: 0.3 g (48%), white solid, m.p.=129.degree. C.-130.degree. C.

$^{1}$H NMR (300 MHz, CDCl$_3$) .delta. (ppm): 14.14 (s, 1H), 8.23 (d, J=2.4 Hz, 1H), 7.67 (dd, J=2.4, 9.0 Hz 1H), 7.13 (d, J=9.0 Hz, 1H), 4.44 (c, J=7.1 Hz, 2H), 4.20 (c, J=7.1 Hz, 2H), 1.42 (t, J=0.5, 7.1 Hz, 3H), 1.24 (t, J=1.5, 7.2 Hz, 3H); .sup.-C NMR (75 MHz, CDCl$_3$) .delta. (ppm): 172.4, 170.4, 158.7, 139.2, 137.0, 128.7, 116.6, 115.7, 114.6, 98.5, 62.5, 37.4, 14.2, 12.7. HPLC: Purity>99%, r.t.=10.6 min. ESI MS (m/z): 342 [M+H].sup.+.

Ethyl 6-chloro-4-hydroxy-1-methyl-2-oxo-1,2-dihydroquinoline-3-carboxylate (37)

Reagents: Comp 24 (3.5 mmols, 0.8 g); Sodium hydride (7.1 mmols, 0.18 g); Diethyl malonate (18 mmols, 2.8 g). Yield: 0.3 g (30%), white solid, m.p.=138.degree. C.-139.degree. C.

$^{1}$H NMR (300 MHz, CDCl$_3$) .delta. (ppm): 14.13 (s, 1H), 8.07 (d, J=2.5 Hz, 1H), 7.55 (dd, J=2.5, 9.0 Hz 1H), 7.20 (d, J=2.0 Hz, 1H), 4.44 (c, J=7.1 Hz, 2H), 3.57 (s, 3H), 1.41 (t, J=7.1 Hz, 3H); .sup.-C NMR (75 MHz, CDCl$_3$) .delta. (ppm): 172.5, 170.6, 159.4, 139.9, 134.4, 127.9, 125.15, 116.1, 115.7, 98.7, 62.6, 29.5, 14.3. HPLC: Purity>96%, r.t.=9.4 min. ESI MS (m/z): 282 [M+H].sup.+.

Ethyl 6-chloro-1-ethyl-4-hydroxy-2-oxo-1,2-dihydroquinoline-3-carboxylate (38)

Reagents: Comp 25 (3.5 mmols, 0.8 g); Sodium hydride (7.4 mmols, 0.17 g); Diethyl malonate (17.7 mmols, 2.8 g). Yield: 0.5 g (48%), white solid, m.p.=140.degree. C.-141.degree. C.

$^{1}$H NMR (300 MHz, CDCl$_3$) .delta. (ppm): 14.14 (s, 1H), 8.09 (d, J=2.5 Hz, 1H), 7.54 (dd, J=2.5, 9.1 Hz 1H), 7.19 (d, J=2.0 Hz, 1H), 4.44 (c, J=7.1 Hz, 2H), 4.21 (c, J=7.1 Hz, 2H), 1.42 (t, J=7.1 Hz, 3H), 1.25 (t, J=7.1 Hz, 3H); .sup.-C NMR (75 MHz, CDCl$_3$) .delta. (ppm): 171.4, 169.5, 157.7, 137.8, 133.3, 126.4, 124.2, 115.1, 114.5, 97.5, 61.2, 36.4, 14.3, 13.2. HPLC: Purity>99%, r.t.=9.9 min. ESI MS (m/z): 296 [M+H].sup.+.

Ethyl 7-chloro-4-hydroxy-1-methyl-2-oxo-1,2-dihydroquinoline-3-carboxylate (39)

Reagents: Comp 26 (2.05 mmols, 0.4 g); Sodium hydride (4.16 mmols, 0.1 g); Diethyl malonate (10.2 mmols, 1.65 g). Yield: 0.28 g (49%), white solid, m.p.=153.degree. C.-154.degree. C.

$^{1}$H NMR (300 MHz, DMSO-d$_6$) .delta. (ppm): 12.95 (s, 1H), 8.02 (d, J=8.6 Hz, 1H), 7.59 (d, J=1.8 Hz, 1H), 7.33 (dd, J=1.9, 8.7 Hz, 1H), 4.32 (c, J=7.1 Hz, 2H), 3.52 (s, 3H), 1.30 (t, J=7.1 Hz, 3H); .sup.-C NMR (75 MHz, DMSO-d$_6$) .delta. (ppm): 168.9, 164.6, 159.2, 141.7, 138.9, 126.7, 122.5, 115.1, 113.7, 102.3, 61.8, 49.1, 29.4, 14.4. HPLC: Purity>99%, r.t.=5.1 min. ESI MS (m/z): 282 [M+H].sup.+.

Ethyl 7-chloro-1-ethyl-4-hydroxy-2-oxo-1,2-dihydroquinoline-3-carboxylate (40)

Reagents: Comp 27 (2.6 mmols, 0.6 g); Sodium hydride (4.6 mmols, 0.11 g); Diethyl malonate (11.5 mmols, 1.85 g). Yield: 0.46 g (62%), yellow solid, m.p.=141.degree. C.-142.degree. C.

$^{1}$H NMR (300 MHz, DMSO-d$_6$) .delta. (ppm): 13.00 (s, 1H), 8.03 (d, J=8.6 Hz, 1H), 7.64 (d, J=1.8 Hz, 1H), 7.33 (dd, J=1.9, 8.6 Hz, 1H), 4.32 (c, J=7.1 Hz, 2H), 4.19 (c, J=7.1 Hz, 2H), 1.30 (t, J=7.1 Hz, 3H), 1.15 (t, J=7.1 Hz, 3H); .sup.-C NMR (75 MHz, DMSO-d$_6$) .delta. (ppm): 169.0, 164.8, 158.6, 140.7, 139.0, 127.0, 122.3, 114.6, 113.9, 102.0, 61.8, 37.1, 14.4, 13.0. HPLC: Purity>99%, r.t.=9.9 min. ESI MS (m/z): 296 [M+H].sup.+.

Ethyl 1-benzyl-7-chloro-4-hydroxy-2-oxo-1,2-dihydroquinoline-3-carboxylate (41)

Reagents: Comp 28 (1.9 mmols, 0.5 g); Sodium hydride (3.96 mmols, 0.09 g); Diethyl malonate (9.6 mmols, 1.55 g). Yield: 0.9 g (94%), white solid, m.p.=172.degree. C.-173.degree. C.

$^{1}$H NMR (300 MHz, DMSO-d$_6$) .delta. (ppm): 13.17 (s, 1H), 8.07 (d, J=8.6 Hz, 1H), 7.43 (d, J=1.8 Hz, 1H), 7.35-7.32 (m, 3H), 7.26-7.23 (m, 1H), 7.18 (dd, J=1.3, 8.6 Hz, 2H), 5.47 (s, 2H), 4.34 (c, J=7.1 Hz, 2H), 1.31 (t, J=7.1 Hz, 3H); .sup.-C NMR (75 MHz, DMSO-d$_6$) .delta. (ppm): 168.5, 164.8, 158.9, 140.6, 138.7, 136.5, 128.7, 127.1, 126.6, 126.4, 122.3, 114.9, 113.8, 101.6, 61.5, 44.5, 13.9. HPLC: Purity>99%, r.t.=10.8 min. ESI MS (m/z): 358 [M+H].sup.+.

General Synthesis Process for Compounds 42-62

The corresponding ethyl carboxylate derivative (compounds 29-41), jointly with the corresponding hydrazide in DMF (0.3 ml), are added in a flask. The mixture is heated to 160.degree. C. for 3 min. The reaction is allowed to cool at room temperature and, subsequently, MeOH is added (5 ml), to form a precipitate that is filtered and purified with MeOH washings.

Diagram 5

-continued

| | | |
|---|---|---|
| R₃ = H | R₁ = isoprenilo | R₂ = ⟋⟍⟋⟍⟋⟍₆ Comp 42 |
| R₃ = H | R₁ = isoprenilo | R₂ = ⟋⟍⟋⟍⟋⟍₁₀ Comp 43 |
| R₃ = H | R₁ = isobutilo | R₂ = ⟋⟍⟋⟍⟋⟍₁₀ Comp 44 |
| R₃ = H | R₁ = CH₂-ciclopropilo | |
| R₃ = H | R₁ = CH₂—Ph | R₂ = ⟋⟍⟋⟍⟋⟍₁₀ Comp 45 |
| R₃ = 6-Br | R₁ = H | |
| R₃ = 6-Cl | R₁ = H | R₂ = ⟋⟍⟋⟍⟋⟍₁₀ Comp 46 |
| R₃ = 6-Br | R₁ = Me | |
| R₃ = 6-Br | R₁ = Me | R₂ = ⟋⟍⟋⟍⟋⟍₁₀ Comp 47 |
| R₃ = 6-Br | R₁ = Et | |
| R₃ = 6-Br | R₁ = Et | R₂ = ⟋⟍⟋⟍⟋⟍₁₀ Comp 48 |
| R₃ = 6-Cl | R₁ = Me | |
| R₃ = 6-Cl | R₁ = Me | R₂ = ⟋⟍⟋⟍⟋⟍₆ Comp 49 |
| R₃ = 6-Cl | R₁ = Et | |
| R₃ = 6-Cl | R₁ = Et | R₂ = ⟋⟍⟋⟍⟋⟍₁₀ Comp 50 |
| R₃ = 7-Cl | R₁ = Me | |
| R₃ = 7-Cl | R₁ = Me | R₂ = ⟋⟍⟋⟍⟋⟍₁₀ Comp 51 |
| R₃ = 7-Cl | R₁ = Et | |
| R₃ = 7-Cl | R₁ = Et | R₂ = ⟋⟍⟋⟍⟋⟍₆ Comp 52 |
| R₃ = 7-Cl | R₁ = CH₂—Ph | |
| R₃ = 7-Cl | R₁ = CH₂—Ph | R₂ = ⟋⟍⟋⟍⟋⟍₁₀ Comp 53 |
| | | R₂ = ⟋⟍⟋⟍⟋⟍₆ Comp 54 |
| | | R₂ = ⟋⟍⟋⟍⟋⟍₆ Comp 55 |
| | | R₂ = ⟋⟍⟋⟍⟋⟍₁₀ Comp 56 |
| | | R₂ = ⟋⟍⟋⟍⟋⟍₆ Comp 57 |
| | | R₂ = ⟋⟍⟋⟍⟋⟍₁₀ Comp 58 |
| | | R₂ = ⟋⟍⟋⟍⟋⟍₆ Comp 59 |
| | | R₂ = ⟋⟍⟋⟍⟋⟍₁₀ Comp 60 |
| | | R₂ = ⟋⟍⟋⟍⟋⟍₆ Comp 61 |
| | | R₂ = ⟋⟍⟋⟍⟋⟍₁₀ Comp 62 |

4-Hydroxy-1-isoprenyl-N'-octanoyl-2-oxo-1,2-dihydroquinoline-3-carbohydrazide (42)

Reagents: Comp 29 (0.66 mmols, 0.2 g); octanoyl hydrazine (0.73 mmols, 0.12 g). Yield: 0.125 g (22%), white solid, m.p.=114.degree. C.-115.degree. C.

.sup.1H NMR (300 MHz, CDCl.sub.3) .delta. (ppm): 15.37 (s, 1H), 12.38 (d, J=5.3 Hz, 1H), 8.67-8.55 (m, 1H), 8.06 (d, J=7.9 Hz, 1H), 7.57 (t, J=7.9 Hz, 1H), 7.22-7.14 (m, 2H), 5.1-5.02 (m, 1H), 4.81-4.76 (m, 2H), 2.26 (t, J=7.5 Hz, 2H), 1.80 (s, 3H).1.7-1.52 (m, 5H), 1.38-1.1 (m, 8H), 0.79 (t, J=6.4 Hz, 3H); .sup.-C NMR (75 MHz, CDCl.sub.3) .delta. (ppm): 170.1, 169.6, 166.9, 161.7, 139.7, 136.5, 134.09, 125.1, 122.4, 119.1, 115.8, 114.9, 96.4, 40.9, 34.4, 31.8, 29.3, 29.1, 25.7, 26.6, 22.7, 18.5, 14.2. HPLC: Purity>99%, r.t.=13.7 min. ESI MS (m/z): 414 [M+H].sup.+. Elementary Analysis (C.sub.23H.sub.13N.sub.3O.sub.4) Calculated: C, 66.81%; H, 7.51%; N, 10.16%. Found: C, 66.73%; H, 7.74%; N, 10.25%.

N'-Dodecanoyl-4-hydroxy-1-isoprenyl-2-oxo-1,2-dihydroquinoline-3-carbohydrazide (43)

Reagents: Comp 29 (0.66 mmols, 0.2 g); dodecanoyl hydrazine (0.73 mmols, 0.16 g). Yield: 0.125 g (40%), white solid, m.p.=107.degree. C.-108.degree. C.

.sup.1H NMR (300 MHz, DMSO-d.sub.6) .delta. (ppm): 16.28 (s, 1H), 11.97 (d, J=3.9 Hz, 1H), 10.77 (d, J=3.9 Hz, 1H), 8.11 (dd, J=7.9, 1.5 Hz, 1H), 7.83 (td, J=9.18, 7.2, 1.6 Hz, 1H), 7.51 (d, J=8.6 Hz, 1H), 7.39 (t, J=8.6 Hz, 1H), 5.51-5.05 (m, 1H), 4.95-4.85 (m, 2H), 2.23 (t, J=7.3 Hz, 2H), 1.85 (s, 3H), 1.67 (s, 3H), 1.6-1.40 (m, 2H), 1.35-1.1 (m, 16H), 0.84 (t, J=6.5 Hz, 3H); .sup.-C NMR (75 MHz, DMSO-d.sub.6) .delta. (ppm): 170.7, 169.6, 167.3, 160.9, 139.0, 135.8, 134.7, 124.7, 122.7, 119.2, 115.5, 114.9, 95.7, 32.9, 31.3, 29.0, 28.9, 28.8, 28.7, 28.5, 25.3, 24.9, 22.1, 18.2, 13.9. HPLC: Purity>99%, r.t.=4.9 min. ESI MS (m/z): 470 [M+2H].sup.+. Elementary Analysis (C.sub.27H.sub.37N.sub.3O.sub.4) Calculated: C, 69.35%; H, 7.98%; N, 8.99%. Found: C, 69.48%; H, 8.01%; N, 8.86%.

N'-Dodecanoyl-4-hydroxy-1-isobutyl-2-oxo-1,2-dihydroquinoline-3-carbohydrazide (44)

Reagents: Comp 30 (0.52 mmols, 0.15 g); dodecanoyl hydrazine (0.78 mmols, 0.17 g). Yield: 0.05 g (21%), white solid, m.p.=112.degree. C.-113.degree. C.

.sup.1H NMR (300 MHz, DMSO-d.sub.6) .delta. (ppm): 16.32 (s, 1H), 12.05 (d, J=4.1 Hz, 1H), 10.79 (d, J=4.1 Hz, 1H), 8.12 (d, J=1.6 Hz, 1H), 7.9-7.75 (m, 1H), 7.70 (d, J=8.5 Hz, 1H), 7.35 (t, J=7.6 Hz, 1H), 4.18 (d, J=7.5 Hz, 2H), 2.30-2.05 (m, 3H), 1.52-1.35 (m, 2H), 1.25-1.05 (m, 16H), 0.95-0.80 (m, 9H); .sup.13C NMR (75 MHz, DMSO-d.sub.6) .delta. (ppm): 170.6, 169.4, 167.0, 161.5, 139.4, 134.5, 124.6, 122.6, 115.9, 114.9, 95.5, 47.85, 31.3, 29.0, 28.9, 28.7, 28.6, 28.5, 26.7, 24.9, 22.0, 19.8, 13.9. HPLC: Purity>97%, r.t.=6.6 min. ESI MS (m/z): 458 [M+H].sup.+. Elementary Analysis (C.sub.26H.sub.39N.sub.3O.sub.4) Calculated: C, 68.24%; H, 8.59%; N, 9.18%. Found: C, 68.33%; H, 8.71%; N, 9.44%.

1-(cyclopropylmethyl)-N'-dodecanoyl-4-hydroxy-2-oxo-1,2-dihydroquinoline-3-carbohydrazide (45)

Reagents: Comp 31 (0.45 mmols, 0.13 g); dodecanoyl hydrazine (0.68 mmols, 0.15 g). Yield: 0.09 g (49%), white solid, m.p.=121.degree. C.-122.degree. C.

.sup.1H NMR (300 MHz, DMSO-d.sub.6) .delta. (ppm): 16.30 (s, 1H), 12.01 (d, J=4.1 Hz, 1H), 10.76 (d, J=4.1 Hz, 1H), 8.12 (d, J=7.9 Hz, 1H), 7.8-7.6 (m, 2H), 7.35 (t, J=7.6 Hz, 1H), 4.23 (d, J=6.9 Hz, 2H), 2.23 (t, J=7.6 Hz, 2H), 1.6-1.42 (m, 2H), 1.32-1.17 (m, 16H), 0.84 (t, J=6.9 Hz, 3H), 0.52-0.42 (m, 5H); .sup.13C NMR (75 MHz, DMSO-d.sub.6) .delta. (ppm): 170.7, 169.5, 167.0, 161.3, 139.3, 134.6, 124.6, 122.7, 115.8, 114.9, 95.6, 45.2, 32.9, 31.3, 29.0, 28.9, 28.8, 28.7, 28.5, 25.0, 22.1, 13.9, 9.8, 3.7. HPLC: Purity>99%, r.t.=15.8 min. ESI MS (m/z): 456 [M+H].sup.+. Elementary Analysis (C.sub.26H.sub.37N.sub.3O.sub.4) Calculated: C, 68.54%; H, 8.19%; N, 9.22%. Found: C, 68.50%; H, 8.28%; N, 9.04%.

1-Benzyl-N'-dodecanoyl-4-hydroxy-2-oxo-1,2-dihydroquinoline-3-carbohydrazide (46)

Reagents: Comp 32 (0.12 mmols, 0.04 g); dodecanoyl hydrazine (0.15 mmols, 0.033 g). Yield: 0.045 g (75%), white solid, m.p.=150.degree. C.-151.degree. C.

¹H NMR (300 MHz, DMSO-d₆) δ (ppm): 15.63 (s, 1H), 12.13 (d, J=4.1 Hz, 1H), 8.25-8.08 (m, 2H), 7.3-7.1 (m, 7H), 5.46 (s, 2H), 2.35-2.10 (m, 2H), 1.75-1.50 (m, 2H), 1.5-1.1 (m, 16H), 0.9-0.75 (m, 3H); ¹³C NMR (75 MHz, DMSO-d₆) δ (ppm): 170.5, 168.2, 165.8, 161.1, 138.7, 134.9, 133.2, 127.9, 126.4, 125.4, 121.6, 114.9, 114.2, 95.1, 44.9, 33.4, 30.9, 28.6, 28.4, 28.3, 28.2, 24.4, 21.7, 13.1. HPLC: Purity>99%, r.t.=9.6 min. ESI MS (m/z): 493 [M+H]⁺. Elementary Analysis (C₂₉H₃₇N₃O₄) Calculated: C, 70.85%; H, 7.59%; N, 8.55%. Found: C, 71.02%; H, 7.70%; N, 8.68%.

6-Bromo-N'-dodecanoyl-4-hydroxy-2-oxo-2-hydroquinoline-3-carbohydrazide (47)

Reagents: Comp 33 (0.25 mmols, 0.07 g); dodecanoyl hydrazine (0.27 mmols, 0.06 g). Yield: 0.103 g (85%), white solid, m.p.=286°C.-287°C.

¹H NMR (300 MHz, DMSO-d₆) δ (ppm): 16.20 (s, 1H), 12.17 (sa, 1H), 11.9 (d, J=4.0 Hz, 1H), 10.76 (d, J=4.1 Hz, 1H), 7.86 (dd, J=8.7 Hz, 1H), 7.33 (d, J=8.9 Hz, 1H), 2.2 (t, J=7.3 Hz, 2H), 1.60-1.42 (m, 2H), 1.2 (s, 16H), 0.84 (t, J=6.6 Hz, 3H); ¹³C NMR (75 MHz, DMSO-d₆) δ (ppm): 170.4, 169.4, 167.0, 161.5, 137.6, 136.0, 134.9, 132.3, 126.0, 125.4, 117.9, 113.8, 32.6, 30.7, 28.4, 28.3, 28.2, 28.1, 28.0, 24.4, 21.4, 13.2. ESI MS (m/z): 481. Elementary Analysis (C₂₂H₃₀BrN₃O₄) Calculated: C, 55.0%; H, 6.29%; N, 8.75%. Found: C, 54.98%; H, 6.57%; N, 8.90%.

6-Chloro-N'-dodecanoyl-4-hydroxy-2-oxo-2-hydroquinoline-3-carbohydrazide (48)

Reagents: Comp 34 (0.14 mmols, 0.037 g); dodecanoyl hydrazine (0.15 mmols, 0.034 g). Yield: 0.045 g (73%), white solid, m.p.=285°C.-286°C.

¹H NMR (300 MHz, DMSO-d₆) δ (ppm): 16.22 (s, 1H), 12.18 (s, 1H), 11.9 (d, J=4.2 Hz, 1H), 10.75 (sa, 1H), 7.97-7.90 (m, 1H), 7.76 (dd, J=2.46, 8.8 Hz, 1H), 7.40 (d, J=8.8 Hz, 1H), 2.2 (t, J=7.3 Hz, 2H), 1.60-1.45 (m, 2H), 1.2 (s, 16H), 0.85 (t, J=6.4 Hz, 3H).

6-Bromo-4-hydroxy-1-methyl-N'-octanoyl-2-oxo-1,2-dihydroquinoline-3-carbohydrazide (49)

Reagents: Comp 35 (0.46 mmols, 0.15 g); octanoyl hydrazine (0.5 mmols, 0.08 g). Yield: 0.13 g (64%), white solid, m.p.=185°C.-186°C.

¹H NMR (300 MHz, DMSO-d₆) δ (ppm): 16.30 (s, 1H), 11.94 (d, J=4.2 Hz, 1H), 10.8 (d, J=4.2 Hz, 1H), 8.12 (s, 1H), 7.95 (d, J=9.3 Hz, 1H), 7.61 (d, J=9.0 Hz, 1H), 3.6 (s, 3H), 2.23 (t, J=7.4 Hz, 2H), 1.6-1.42 (m, 2H), 1.27 (s, 8H), 0.86 (t, J=6.2 Hz, 3H); ¹³C NMR (75 MHz, DMSO-d₆) δ (ppm): 169.4, 169.3, 166.8, 160.8, 138.7, 136.4, 126.0, 117.7, 116.2, 114.5, 96.3, 32.7, 30.8, 29.2, 28.2, 27.9, 24.6, 21.6, 13.5. HPLC: Purity>98%, r.t.=9.8 min. ESI MS (m/z): 440 [M+H]⁺. Elementary Analysis (C₁₉H₂₄BrN₃O₄) Calculated: C, 52.0%; H, 5.52%; N, 9.59%. Found: C, 52.06%; H, 5.50%; N, 9.77%.

6-Bromo-N'-dodecanoyl-4-hydroxy-1-methyl-2-oxo-1,2-dihydroquinoline-3-carbohydrazide (50)

Reagents: Comp 35 (0.36 mmols, 0.12 g); dodecanoyl hydrazine (0.4 mmols, 0.08 g). Yield: 0.1 g (55%), white solid, m.p.=160°C.-161°C.

¹H NMR (300 MHz, DMSO-d₆) δ (ppm): 16.23 (s, 1H), 11.85 (sa, J=4.3 Hz, 1H), 10.5 (sa, J=5.5 Hz, 1H), 8.14 (d, J=2.2 Hz, 1H), 7.91 (dd, J=9.1, 1.4 Hz, 1H), 7.58 (d, J=9.1 Hz, 1H), 3.6 (s, 3H), 2.26 (t, J=7.4 Hz, 2H), 1.6-1.45 (m, 2H), 1.27 (s, 16H), 0.87 (t, J=6.4 Hz, 3H); ¹³C NMR (75 MHz, DMSO-d₆) δ (ppm): 170.4, 167.8, 161.8, 139.7, 137.4, 127.0, 118.6, 117.3, 115.4, 97.2, 32.6, 30.7, 28.9, 28.5, 28.4, 28.2, 28.0, 24.4, 21.5, 13.2. HPLC: Purity>98%, r.t.=14.3 min. ESI MS (m/z): 494 [M+H]⁺. Elementary Analysis (C₂₃H₃₂BrN₃O₄) Calculated: C, 55.8%; H, 6.52%; N, 8.50%. Found: C, 55.94%; H, 6.80%; N, 8.61%.

6-Bromo-1-ethyl-4-hydroxy-N'-octanoyl-2-oxo-1,2-dihydroquinoline-3-carbohydrazide (51)

Reagents: Comp 36 (0.36 mmols, 0.12 g); octanoyl hydrazine (0.4 mmols, 0.06 g). Yield: 0.13 g (80%), white solid, m.p.=171°C.-172°C.

¹H NMR (300 MHz, DMSO-d₆) δ (ppm): 16.24 (s, 1H), 11.88 (d, J=4.0 Hz. 1H), 10.6 (d, J=4.1 Hz, 1H), 8.12 (d, J=2.5 Hz, 1H), 7.90 (dd, J=9.1, 2.5 Hz, 1H), 7.61 (d, J=9.1 Hz, 1H), 4.3 (c, J=7.0 Hz, 2H), 2.22 (t, J=7.4 Hz, 2H), 1.57-1.50 (m, 2H), 1.30-1.17 (m, 11H), 0.84 (t, J=6.7 Hz, 3H); ¹³C NMR (75 MHz, DMSO-d₆) δ (ppm): 169.4, 166.7, 160.4, 137.8, 136.7, 126.3, 117.5, 116.6, 114.4, 96.2, 36.9, 32.8, 30.9, 28.3, 28.1, 24.7, 21.7, 13.6, 12.4. HPLC: Purity>98%, r.t.=13.5 min. ESI MS (m/z): 452 [M+H]⁺.

6-Bromo-N'-dodecanoyl-1-ethyl-4-hydroxy-2-oxo-1,2-dihydroquinoline-3-carbohydrazide (52)

Reagents: Comp 36 (0.36 mmols, 0.12 g); dodecanoyl hydrazine (0.4 mmols, 0.08 g). Yield: 0.15 g (80%), white solid, m.p.=146°C.-147°C.

¹H NMR (300 MHz, DMSO-d₆) δ (ppm): 16.28 (s, 1H), 11.97 (s, 1H), 10.8 (s, 1H), 8.16 (s, 1H), 7.97 (dd, J=9.6, 2.5 Hz, 1H), 7.62 (d, J=8.8 Hz, 1H), 4.3 (c, J=6.9 Hz, 2H), 2.24 (t, J=7.2 Hz, 2H), 1.6-1.45 (m, 2H), 1.26 (s, 19H), 0.85 (t, J=8.6 Hz, 3H); ¹³C NMR (75 MHz, DMSO-d₆) δ (ppm): 169.3, 166.7, 160.3, 137.6, 136.4, 126.2, 117.2, 116.5, 114.2, 96.0, 36.7, 32.6, 30.8, 28.5, 28.4, 28.2, 28.1, 28.0, 24.4, 21.5, 13.2, 12.1. HPLC: Purity>98%, r.t.=6.2 min. ESI MS (m/z): 510 [M+2H]⁺. Elementary Analysis (C₂₄H₃₄BrN₃O₄) Calculated: C, 56.7%; H, 6.74%; N, 8.26%. Found: C, 56.75%; H, 7.01%; N, 8.43%.

6-Chloro-4-hydroxy-1-methyl-N'-octanoyl-2-oxo-1,2-dihydroquinoline-3-carbohydrazide (53)

Reagents: Comp 37 (0.36 mmols, 0.1 g); octanoyl hydrazine (0.39 mmols, 0.062 g). Yield: 0.12 g (86%), white solid, m.p.=187°C.-188°C.

¹H NMR (300 MHz, DMSO-d₆) δ (ppm): 16.33 (s, 1H), 11.96 (d, J=4.2 Hz, 1H), 10.8 (d, J=4.2 Hz, 1H), 8.06 (d, J=2.6 Hz, 1H), 7.86 (dd, J=9.0, 2.5 Hz, 1H), 7.68 (d, J=9.1 Hz, 1H), 3.6 (s, 3H), 2.24 (t, J=7.4 Hz, 2H), 1.6-1.45 (m, 2H), 1.26 (s, 16H), 0.87 (t, J=6.2 Hz, 3H); ¹³C NMR (75 MHz, DMSO-d₆) δ (ppm): 169.4, 166.8, 161.1, 160.8, 138.4, 133.7, 126.9, 122.9, 117.5, 115.9, 96.2, 32.7, 30.8, 29.2, 28.2, 28.0, 24.6, 21.6, 13.5. HPLC: Purity>97%, r.t.=12.3 min. ESI MS (m/z): 394 [M+H]⁺. Elementary Analysis (C₁₉H...

6-Chloro-N'-dodecanoyl-4-hydroxy-1-methyl-2-oxo-1,2-dihydroquinoline-3-carbohydrazide (54)

Reagents: Comp 37 (0.36 mmols, 0.10 g); dodecanoyl hydrazine (0.39 mmols, 0.08 g). Yield: 0.143 g (90%), white solid, m.p.=156.5°C.-157.5°C.

$^1$H NMR (300 MHz, DMSO-$d_6$) δ (ppm): 16.33 (s, 1H), 11.96 (d, J=4.2 Hz, 1H), 10.8 (d, J=4.2 Hz, 1H), 8.00 (d, J=2.5 Hz, 1H), 7.86 (dd, J=9.1, 2.5 Hz, 1H), 7.69 (d, J=9.1 Hz, 1H), 3.6 (s, 3H), 2.23 (t, J=7.3 Hz, 2H), 1.6-1.47 (m, 2H), 1.25 (s, 16H), 0.85 (t, J=6.4 Hz, 3H); $^{13}$C NMR (75 MHz, DMSO-$d_6$) δ (ppm): 169.6, 169.4, 166.8, 160.8, 138.4, 133.7, 126.9, 122.9, 117.5, 115.8, 96.2, 32.9, 29.2, 28.6, 28.5, 28.3, 28.3, 28.2, 24.6, 21.7, 13.5. HPLC: Purity>99%, r.t.=13.9 min. ESI MS (m/z): 450 [M+H]$^+$. Elementary Analysis ($C_{23}H_{32}ClN_3O_4$) Calculated: C, 61.39%; H, 7.17%; N, 9.34%. Found: C, 61.46%; H, 7.44%; N, 9.60%.

6-Chloro-1-ethyl-4-hydroxy-N'-octanoyl-2-oxo-1,2-dihydroquinoline-3-carbohydrazide (55)

Reagents: Comp 38 (0.68 mmols, 0.2 g); octanoyl hydrazine (0.74 mmols, 0.119 g). Yield: 0.19 g (70%), white solid, m.p.=160°C.-161°C.

$^1$H NMR (300 MHz, DMSO-$d_6$) δ (ppm): 16.33 (s, 1H), 11.98 (d, J=4.1 Hz, 1H), 10.8 (d, J=4.1 Hz, 1H), 8.03 (d, J=2.3 Hz, 1H), 7.86 (dd, J=9.2, 2.6 Hz, 1H), 7.75 (d, J=9.2 Hz, 1H), 4.3 (c, J=6.9 Hz, 2H), 2.24 (t, J=7.3 Hz, 2H), 1.60-1.53 (m, 2H), 1.35-1.18 (m, 11H), 0.87 (t, J=6.4 Hz, 3H); $^{13}$C NMR (100 MHz, DMSO-$d_6$) δ (ppm): 170.3, 166.6, 161.3, 138.2, 134.8, 127.7, 124.2, 118.2, 117.0, 97.1, 39.8, 37.8, 33.6, 31.7, 29.2, 28.9, 25.6, 22.6, 14.5, 13.3. HPLC: Purity>98%, r.t.=13.1 min. ESI MS (m/z): 408 [M+H]$^+$. Elementary Analysis ($C_{20}H_{26}ClN_3O_4$) Calculated: C, 58.89%; H, 6.42%; N, 10.30%. Found: C, 59.11%; H, 6.38%; N, 10.50%.

6-Chloro-N'-dodecanoyl-1-ethyl-4-hydroxy-2-oxo-1,2-dihydroquinoline-3-carbohydrazide (56)

Reagents: Comp 36 (0.68 mmols, 0.2 g); dodecanoyl hydrazine (0.75 mmols, 0.16 g). Yield: 0.234 g (74%), white solid, m.p.=149°C.-150°C.

$^1$H NMR (300 MHz, DMSO-$d_6$) δ (ppm): 16.3 (s, 1H), 11.9 (d, J=4.2 Hz, 1H), 10.8 (d, J=4.2 Hz, 1H), 8.05 (d, J=2.6 Hz, 1H), 7.97 (dd, J=9.1, 2.6 Hz, 1H), 7.62 (d, J=9.2 Hz, 1H), 4.3 (c, J=6.9 Hz, 2H), 2.23 (t, J=7.3 Hz, 2H), 1.35-1.17 (m, 19H), 0.86 (t, J=7.4 Hz, 3H); $^{13}$C NMR (75 MHz, DMSO-$d_6$) δ (ppm): 169.2, 166.6, 160.3, 137.2, 133.6, 126.6, 123.1, 117.0, 116.0, 96.1, 36.8, 32.6, 30.8, 28.5, 28.5, 28.4, 28.2, 28.1, 28.0, 24.5, 21.5, 13.2, 12.1. HPLC: Purity>98%, r.t.=14.9 min. ESI MS (m/z): 464 [M+H]$^+$. Elementary Analysis ($C_{24}H_{34}ClN_3O_4$) Calculated: C, 62.12%; H, 7.39%; N, 9.06%. Found: C, 61.94%; H, 7.61%; N, 9.18%.

7-Chloro-4-hydroxy-1-methyl-N'-octanoyl-2-oxo-1,2-dihydroquinoline-3-carbohydrazide (57)

Reagents: Comp 39 (0.36 mmols, 0.1 g); octanoyl hydrazine (0.39 mmols, 0.063 g). Yield: 0.07 g (50%), white solid, m.p.=164°C.-165°C.

$^1$H NMR (300 MHz, DMSO-$d_6$) δ (ppm): 16.31 (s, 1H), 11.89 (sa, 1H), 10.5 (sa, 1H), 8.09 (dd, J=8.6, 2.5 Hz, 1H), 7.72-7.70 (m, 1H), 7.43-7.40 (m, 1H), 3.64 (s, 3H), 2.25 (t, J=7.4 Hz, 2H), 1.6-1.42 (m, 2H), 1.29 (s, 8H), 0.88 (t, J=6.6 Hz, 3H); $^{13}$C NMR (75 MHz, DMSO-$d_6$) δ (ppm): 170.1, 169.5, 167.0, 161.1, 140.6, 139.2, 126.0, 122.6, 115.0, 113.5, 95.7, 32.7, 30.8, 29.2, 29.1, 28.2, 28.0, 24.6, 21.7, 13.5. HPLC: Purity>99%, r.t.=7.5 min. ESI MS (m/z): 394 [M+H]$^+$. Elementary Analysis ($C_{16}H_{24}ClN_3O_4$) Calculated: C, 57.94%; H, 6.14%; N, 10.67%. Found: C, 57.85%; H, 6.42%; N, 10.88%.

7-Chloro-N'-dodecanoyl-4-hydroxy-1-methyl-2-oxo-1,2-dihydroquinoline-3-carbohydrazide (58)

Reagents: Comp 39 (0.36 mmols, 0.10 g); dodecanoyl hydrazine (0.39 mmols, 0.08 g). Yield: 0.105 g (65%), white solid, m.p.=165°C.-166°C.

$^1$H NMR (300 MHz, DMSO-$d_6$) δ (ppm): 16.30 (s, 1H), 11.89 (sa, 1H), 10.8 (sa, 1H), 8.06 (d, J=8.6 Hz, 1H), 7.74 (d, J=1.6 Hz, 1H), 7.69 (dd, J=8.6, 1.7 Hz, 1H), 3.6 (s, 3H), 2.23 (t, J=7.2 Hz, 2H), 1.53-1.27 (m, 2H), 1.23 (s, 16H), 0.84 (t, J=6.5 Hz, 3H); $^{13}$C NMR (75 MHz, DMSO-$d_6$) δ (ppm): 170.0, 169.4, 166.9, 161.0, 140.6, 139.1, 126.0, 122.6, 114.9, 113.5, 113.4, 32.7, 30.9, 29.2, 29.1, 28.6, 28.5, 28.3, 28.3, 28.2, 24.6, 21.7, 13.5. HPLC: Purity>98%, r.t.=13.8 min. ESI MS (m/z): 450 [M+H]$^+$. Elementary Analysis ($C_{23}H_{32}ClN_3O_4$) Calculated: C, 61.39%; H, 7.17%; N, 9.34%. Found: C, 61.12%; H, 7.19%; N, 9.61%.

7-Chloro-1-ethyl-4-hydroxy-N'-octanoyl-2-oxo-1,2-dihydroquinoline-3-carbohydrazide (59)

Reagents: Comp 40 (0.5 mmols, 0.15 g); octanoyl hydrazine (0.55 mmols, 0.09 g). Yield: 0.06 g (29%), white solid, m.p.=161°C.-162°C.

$^1$H NMR (300 MHz, DMSO-$d_6$) δ (ppm): 16.31 (s, 1H), 11.91 (d, J=4.1 Hz, 1H), 10.8 (d, J=4.1 Hz, 1H), 8.09 (d, J=8.6 Hz, 1H), 7.90 (d, J=1.9 Hz, 1H), 7.61 (dd, J=8.6, 1.8 Hz, 1H), 4.3 (c, J=7.0 Hz, 2H), 2.23 (t, J=7.3 Hz, 2H), 1.60-1.45 (m, 2H), 1.35-1.12 (m, 11H), 0.86 (t, J=6.6 Hz, 3H); $^{13}$C NMR (75 MHz, DMSO-$d_6$) δ (ppm): 170.0, 169.4, 166.9, 160.7, 139.5, 139.3, 126.3, 122.6, 114.6, 113.7, 95.6, 36.9, 32.7, 30.8, 28.2, 28.0, 24.6, 21.6, 13.5, 12.3. HPLC: Purity>99%, r.t.=8.2 min. ESI MS (m/z): 408 [M+H]$^+$. Elementary Analysis ($C_{20}H_{26}ClN_3O_4$) Calculated: C, 58.9%; H, 6.42%; N, 10.30%. Found: C, 59.13%; H, 6.70%; N, 10.58%.

7-Chloro-N'-dodecanoyl-1-ethyl-4-hydroxy-2-oxo-1,2-dihydroquinoline-3-carbohydrazide (60)

Reagents: Comp 40 (0.5 mmols, 0.15 g); dodecanoyl hydrazine (0.56 mmols, 0.124 g). Yield: 0.221 g (95%), white solid, m.p.=138°C.-139°C.

$^1$H NMR (300 MHz, DMSO-$d_6$) δ (ppm): 16.17 (s, 1H), 11.91 (sa, 1H), 10.8 (sa, 1H), 8.11 (d, J=8.6 Hz, 1H), 7.75 (d, J=1.8 Hz, 1H), 7.42 (dd, J=8.6, 1.8 Hz, 1H), 4.3 (c, J=6.9 Hz, 2H), 2.23 (t, J=7.2 Hz, 2H), 1.54-1.40 (m, 2H), 1.37-1.10 (m, 19H), 0.84 (t, J=6.3 Hz, 3H); $^{13}$C NMR (75 MHz, DMSO-$d_6$) δ (ppm): 169.9, 169.3, 166.7, 160.6, 139.4, 139.2, 126.2, 122.4, 114.3, 113.7, 95.5, 36.7, 32.6, 30.8, 28.5, 28.4, 28.3, 28.2, 24.5, 21.6, 13.3, 12.1.

HPLC: Purity>98%, r.t.=14.7 min. ESI MS (m/z): 464 [M+H].sup.+. Elementary Analysis (C.sub.24H.sub.34ClN.sub.3O.sub.4) Calculated: C, 62.1%; H, 7.39%; N, 9.06%. Found: C, 62.33%; H, 7.57%; N, 9.24%.

1-Benzyl-7-chloro-4-hydroxy-N'-octanoyl-2-oxo-1,2-di hydroquinoline-3-carbohydrazide (61)

Reagents: Comp 41 (0.5 mmols, 0.20 g); octanoyl hydrazine (0.62 mmols, 0.100 g). Yield: 0.196 g (74%), white solid, m.p.=182.degree. C.-183.degree. C.

.sup.1H NMR (300 MHz, DMSO-d.sub.6) .delta. (ppm): 16.51 (s, 1H), 11.86 (d, J=4.2 Hz, 1H), 10.8 (d, J=4.2 Hz, 1H), 8.11 (d, J=8.6 Hz, 1H), 7.57 (d, J=1.8 Hz, 1H), 7.42 (dd, J=8.6, 1.8 Hz, 1H), 7.36-7.30 (m, 2H), 7.28-7.20 (m, 3H), 5.6 (s, 2H), 2.24 (t, J=7.4 Hz, 2H), 1.60-1.50 (m, 2H), 1.35-1.15 (m, 8H), 0.86 (t, J=6.8 Hz, 3H); .sup.13C NMR (75 MHz, DMSO-d.sub.6) .delta. (ppm): 170.7, 169.6, 166.9, 161.5, 140.1, 139.3, 136.1, 128.7, 127.3, 126.7, 126.4, 123.2, 115.5, 114.1, 95.8, 44.8, 32.9, 31.2, 28.5, 28.4, 24.9, 22.1, 13.9. HPLC: Purity>98%, r.t.=2.4 min. ESI MS (m/z): 470 [M+H].sup.+. Elementary Analysis (C.sub.25H.sub.28ClN.sub.3O.sub.4) Calculated: C, 63.89%; H, 6.01%; N, 8.94%. Found: C, 63.47%; H, 6.30%; N, 9.08%.

1-Benzyl-7-chloro-N'-dodecanoyl-4-hydroxy-2-oxo-1,2-dihydroquinoline-3-carbohydrazide (62)

Reagents: Comp 41 (0.56 mmols, 0.20 g); dodecanoyl hydrazine (0.62 mmols, 0.133 g). Yield: 0.25 g (85%), white solid, m.p.=167.degree. C.-168.degree. C.

.sup.1H NMR (300 MHz, DMSO-d.sub.6) .delta. (ppm): 16.49 (s, 1H), 11.87 (d, J=4.2 Hz, 1H), 10.87 (d, J=4.2 Hz, 1H), 8.11 (d, J=8.6 Hz, 1H), 7.57 (d, J=1.8 Hz, 1H), 7.41 (dd, J=8.6, 1.8 Hz, 1H), 7.36-7.30 (m, 2H), 7.28-7.20 (m, 3H), 5.6 (s, 2H), 2.23 (t, J=7.3 Hz, 2H), 1.60-1.50 (m, 2H), 1.30-1.10 (m, 16H), 0.84 (t, J=6.8 Hz, 3H); .sup.13C NMR (75 MHz, DMSO-d.sub.6) .delta. (ppm): 170.7, 169.5, 166.9, 161.5, 140.1, 139.3, 136.1, 128.7, 127.2, 126.6, 126.4, 123.2, 115.5, 114.1, 95.8, 44.8, 32.9, 31.3, 29.0, 28.9, 28.7, 28.7, 28.5, 24.9, 22.1, 13.9. HPLC: Purity>99%, r.t.=5.1 min. ESI MS (m/z): 526 [M+H].sup.+. Elementary Analysis (C.sub.29H.sub.36ClN.sub.3O.sub.4) Calculated: C, 66.21%; H, 6.90%; N, 7.99%. Found: C, 66.21%; H, 7.06%; N, 8.12%.

Synthesis of N'-1-dibenzyl-N'-dodecanoyl-4-hydroxy-2-oxo-1,2-dihydroquinoline-3-carbohydrazide (Comp 63)

Diagram 6

Comp 13

-continued

Comp 63

A mixture containing benzyl bromide (1.88 mmols, 0.32 g), cesium carbonate (1.88 mmol, 0.363 g) and Compound 13 (1.24 mmol, 0.5 g) in DMF (2 ml) is microwave-heated for 1 h at 160.degree. C.

Dichloromethane (25 ml) and water (25 ml) are added to the mixture. The organic phase is separated, and the aqueous phase is once again extracted with dichloromethane (25 ml). The organic phases are brought together and washed with a saturated NaCl solution (30 ml). The organic phase is dried on anhydrous magnesium sulfate and filtered, and the solvent is evaporated under vacuum. The resulting solid is purified by means of silica gel plates using Ethyl acetate:hexane (1:20) as the eluents. A white solid is obtained, 11 mg (2%).

.sup.1H NMR (300 MHz, DMSO-d.sub.6) .delta. (ppm): 15.94 (s, 1H), 11.80 (s, 1H), 8.13 (d, J=8.0 Hz, 1H), 7.73 (t, J=7.8 Hz, 1H), 7.48 (d, J=8.7 Hz, 1H), 7.58-7.30 (m, 11H), 5.5 (s, 2H), 4.77 (s, 2H), 2.36 (t, J=7.4 Hz, 2H), 1.70-1.52 (m, 2H), 1.43-1.2 (m, 16H), 0.81 (t, J=7.6 Hz, 3H); .sup.-C NMR (75 MHz, DMSO-d.sub.6) .delta. (ppm): 173.9, 171.5, 170.6, 161.5, 139.4, 136.4, 136.3, 134.9, 128.7, 128.5, 128.2, 127.4, 127.2, 126.5, 114.9, 96.0, 50.45, 44.8, 31.5, 31.3, 29.0, 28.9, 28.7, 28.5, 24.2, 22.1, 14.0. HPLC: Purity>99%, r.t.=14.6 min. ESI MS (m/z): 582 [M+H].sup.+.

Measurement of the Inhibition of GSK-3.Beta.

The enzyme inhibition assays were performed using the luminometric methodology of Kinase-Glo®. The recombinant human GSK3 enzyme (catalogue no. 14-306) was acquired from Upstate (Dundee, UK). The prephosphorylated polypeptide was synthesised by American Peptide Inc. (Sunnyvale, Calif.). The luminescent kinase kit (catalogue no. V6711) was obtained from Promega. The ATP and the other reagents were purchased from Sigma-Aldrich (St. Louis, Mo.).

The assays were performed in buffer using 96-well plates. 10 .mu.l of the compound to be assayed (dissolved in DMSO at a concentration of 1 mM, and, in turn, dissolved in buffer to the concentration necessary for the experiment) and 10 .mu.l (20 ng) of the enzyme are added to each well, followed by 20 .mu.l of buffer containing 25 .mu.M of the substrate and 1 .mu.M of ATP. The final concentration of DMSO in the experiment did not exceed 1%. Following a half-hour incubation at 30.degree. C., the enzymatic reaction is stopped with 40 .mu.l of the Kinase-Glo® reagent. The luminescence is measured after ten minutes, using a POLARstar Optima multimode reader. The activity is proportional to the difference between the total ATP and the ATP consumed. The inhibitory activities were calculated as a function of the maximum activity, measured in the absence of inhibitor.

TABLE 1

Inhibitory concentration 50 (IC50) of some of the compounds with the formula (I)

| Compound | IC50 GSK-3β (μM) |
|---|---|
| 3 | 8.67 ± 0.40 |
| 4 | 7.35 ± 0.23 |
| 6 | 2.85 ± 0.36 |
| 13 | 4.47 ± 0.29 |
| 14 | 9.00 ± 0.30 |
| 15 | 3.12 ± 0.03 |
| 17 | 5.81 ± 0.76 |
| 42 | 7.11 ± 0.25 |
| 43 | 7.78 ± 0.15 |
| 45 | 5.25 ± 0.58 |
| 46 | 5.51 ± 0.27 |
| 47 | 3.54 ± 0.18 |
| 48 | 3.81 ± 0.12 |
| 49 | 6.28 ± 0.33 |
| 50 | 4.28 ± 0.50 |
| 51 | 7.34 ± 0.20 |
| 52 | 2.01 ± 0.18 |
| 53 | 8.48 ± 0.30 |
| 54 | 5.95 ± 0.49 |
| 55 | 9.42 ± 0.23 |
| 56 | 3.18 ± 0.28 |
| 57 | 6.66 ± 0.29 |
| 58 | 4.03 ± 0.19 |
| 59 | 4.83 ± 0.23 |
| 60 | 2.48 ± 0.26 |
| 61 | 5.96 ± 0.17 |
| 62 | 5.99 ± 0.22 |
| 63 | 6.84 ± 0.51 |

Kinetic Studies on the Inhibition of GSK-3.Beta.

In order to determine the binding mode of these compounds, different kinetic studies were performed, varying the reaction times and the ATP concentration and the substrate concentration. Thus, when the kinetic study is performed at different enzyme incubation times with inhibitor 6 and at two different inhibitor concentrations, it may be observed that the % of enzyme inhibition does not vary; therefore, we may conclude that it is a reversible inhibitor.

TABLE 2

Study of the inhibition of GSK-3.beta. by compound 6 as a function of time.

| Pre-incubation time | [Comp. 6] 10 μM | | [Comp. 6] 5 μM | |
|---|---|---|---|---|
| E + I (min) | % inhibition | deviation | % inhibition | deviation |
| 0 | 61.400072 | 3.68932987 | 27.4181566 | 0.94012209 |
| 5 | 63.0369001 | 5.63307429 | 30.3138744 | 4.02663481 |
| 10 | 62.2631193 | 1.73621051 | 30.1825742 | 1.13957388 |

Figure 1:
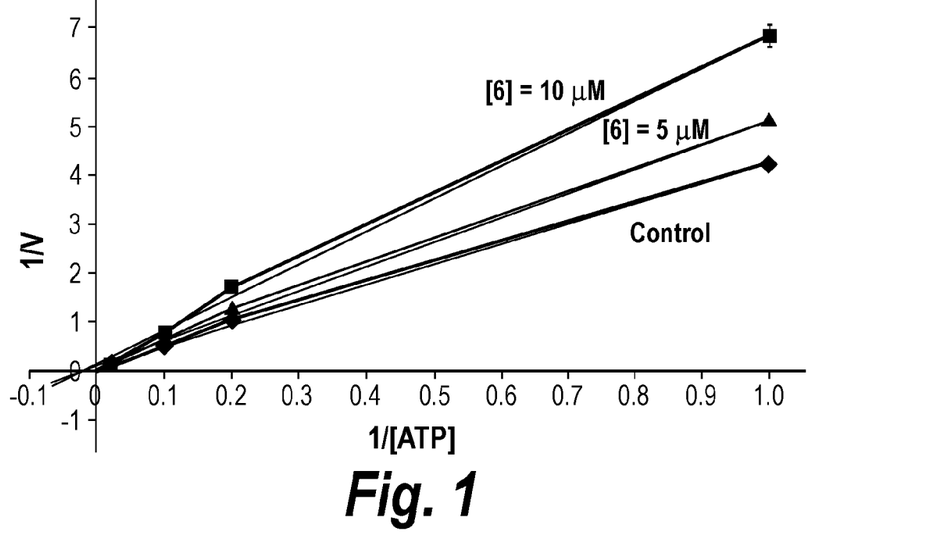
FIG. 1 shows the double-reciprocal plot. The ATP concentrations were varied from 1 to 50 .mu.M, whereas the concentration of the GS-2 peptide was kept constant at 12.5 .mu.M. The concentrations of inhibitor (compound 6) used are shown in the plot.

The kinetic studies conducted by varying the ATP concentration from 1 to 50 .mu.M, and the concentration of inhibitor 6 from 5 to 10 .mu.M, were performed using the ADP-Glo™ Kinase Assay. The double-reciprocal plot (FIG. 1) shows that the intercept on the vertical axis (1V) increases when the concentration of compound 6 increases (from 5 to 10 .mu.M), whereas the intercept on the horizontal axis (1[ATP]) does not change. This means that, whereas the maximum enzyme activity (Vmax) decreases in the presence of the inhibitor, the Michaelis-Menten constant (Km) remains invariable. These results are compatible with the fact that 6 acts as a non-ATP-competitive inhibitor of GSK-3.beta., since an increase in the ATP concentration (from 1 to 50 .mu.M) does not interfere with the enzyme inhibition.

Figure 2:
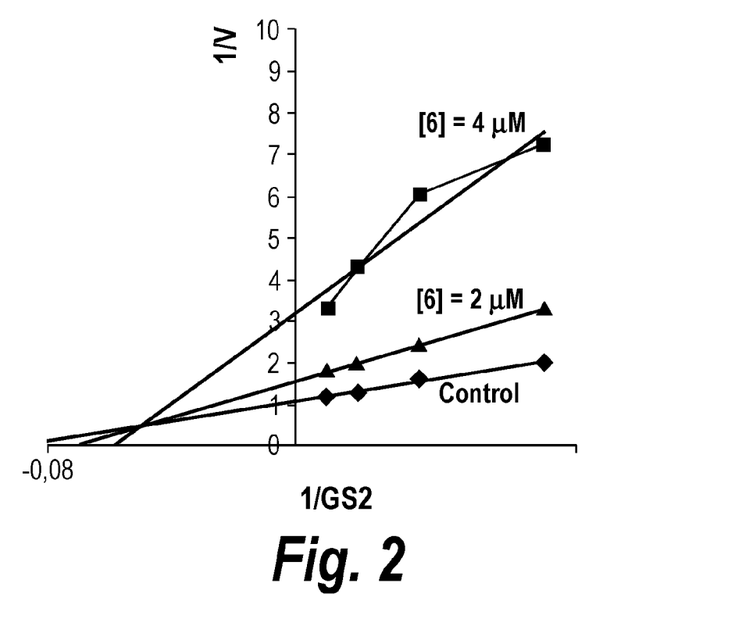
FIG. 2 shows the double-reciprocal plot. The GS-2 concentrations were varied from 15.5 to 100 .mu.M, whereas the ATP concentration was kept constant at 1 .mu.M. The concentrations of inhibitor (compound 6) used are shown in the plot.
Figure 3:
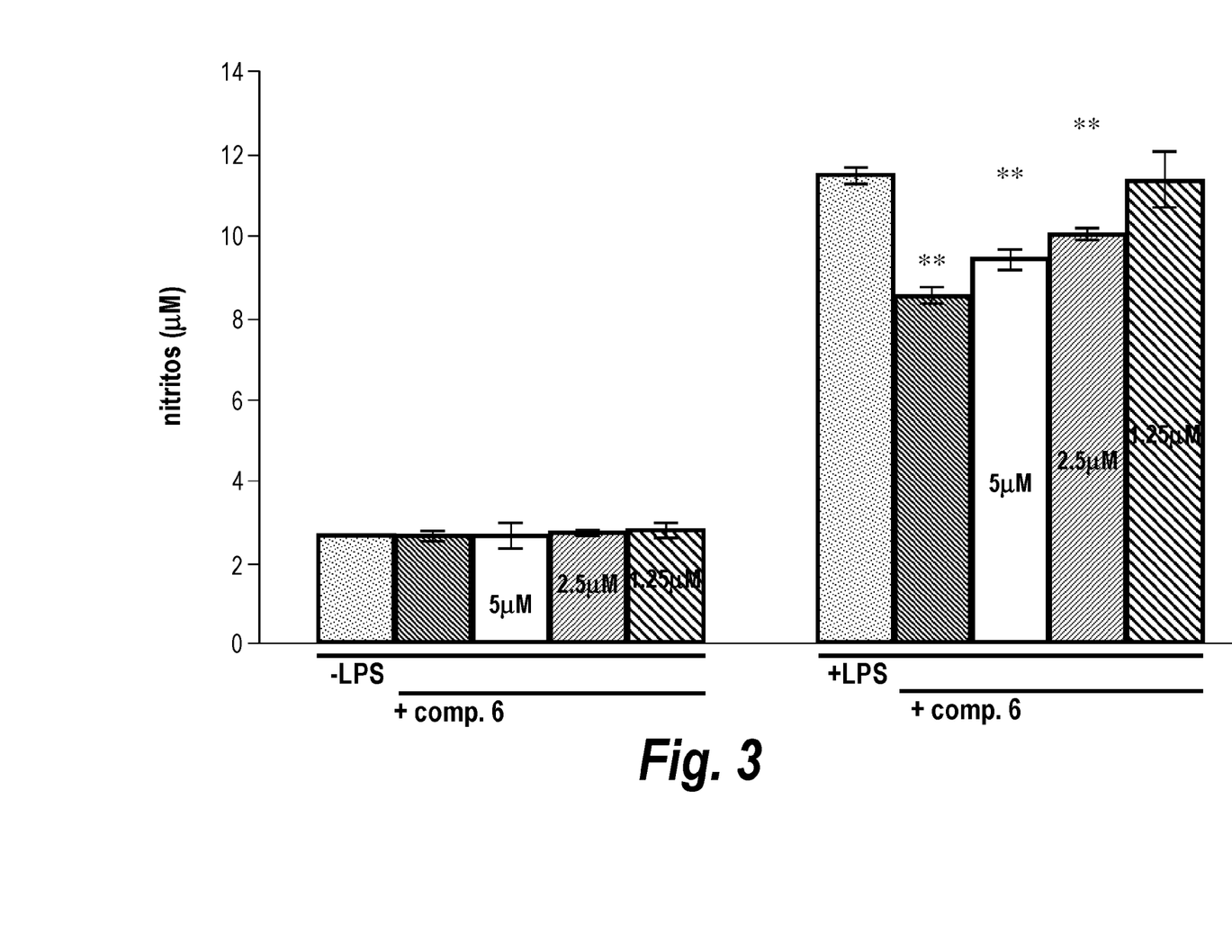
FIG. 3 shows the decrease in inflammatory activity in cell cultures in the presence of variable concentrations of compound 6.

On the other hand, we also studied the dependence of GSK-3.beta. activity in the presence of these inhibitors as a function of the concentration of the substrate, the GS-2 peptide, used in the assays. In these kinetic studies, the GS-2 concentration was varied from 15.5 to 100 .mu.M and the ATP concentration was kept constant at 1 .mu.M. The double-reciprocal plot (FIG. 2) once again shows that the intercept on the vertical axis (1V) increases when the concentration of compound 6 increases (from 5 to 10 .mu.M), whereas the intercept on the horizontal axis (1[GS-2]) does not change. This means that, whereas the maximum enzyme activity (Vmax) decreases in the presence of the inhibitor, the Michaelis-Menten constant (Km) remains invariable. These results are compatible with the fact that compound 6 acts as a substrate-non-competitive inhibitor of GSK-3.beta., since an increase in the GS-2 concentration (from 15.5 to 100 .mu.M) does not interfere with the enzyme inhibition.

All the enzymatic studies, both the activity level studies and the kinetic studies, described herein are compatible with allosteric modulation of the GSK-3.beta. enzyme by these inhibitors.

Determination of the Anti-Inflammatory Activity in Cellular Models

A monolayer culture of RAW 264.7 cells growing in 96-well plates is used. The cells are treated for 1 h with the compounds evaluated. Subsequently, the inflammatory activity is stimulated with 0.4 .mu.g/ml of LPS for 24 h. Once this time has elapsed, the production of nitrites is evaluated by means of the Griess method. Briefly, 50 .mu.l of supernatant are transferred to 96-well plates and 50 .mu.l of Griess reagent are added. The mixture is incubated for 15 minutes at room temperature and the absorbance at 520 nm is measured in a microplate reader.

In order to determine the capacity of the allosteric GSK-3.beta. inhibitors to reduce the activation of inflammation in cell cultures, compound 6 was evaluated at various concentrations (1.25, 2.5, 5 and 10 .mu.M), and a dose-dependent effect on the decrease in nitrite release was found.

The invention claimed is:

1. A pharmaceutical composition comprising a compound with the formula (II)

or the salts, solvates or stereoisomers thereof,
where $R_1$ is selected from H, an optionally substituted $C_1$-$C_5$ alkyl group or an optionally substituted $C_2$-$C_5$ alkenyl group, $R_2$ is an optionally substituted $C_5$-$C_{15}$ alkyl group, $R_3$ is a halogen, n is a value between 1 and 4, $R_4$, $R_5$ and $R_6$ are independently selected from H or an optionally substituted $C_1$-$C_5$ alkyl group,
and a pharmaceutically adequate vehicle.

2. The pharmaceutical composition according to claim 1, where $R_4$, $R_5$ and $R_6$ are H.

3. The pharmaceutical composition according to claim 1, where $R_1$ is selected from H, optionally substituted methyl, ethyl or isobutyl, or $C_5$ alkenyl, preferably isoprenyl.

4. The pharmaceutical composition according to claim 3, where $R_1$ is methyl substituted by cyclopropyl or phenyl.

5. The pharmaceutical composition according to claim 1, where $R_2$ is selected from a $C_{11}$ alkyl group or a $C_7$ alkyl group.

6. The pharmaceutical composition according to claim 1, where $R_3$ is selected from bromine, chlorine or fluorine.

7. The pharmaceutical composition according to claim 6, where n is 1.

8. The pharmaceutical composition according to claim 1, where the compound of formula (II) is selected from the following group:
- 7-Chloro-4-hydroxy-N'-octanoyl-2-oxo-2-hydroquinoline-3-carbohydrazide
- 7-Chloro-N'-dodecanoyl-4-hydroxy-2-oxo-2-hydroquinoline-3-carbohydrazide
- 6-Fluoro-N'-dodecanoyl-4-hydroxy-2-oxo-2-hydroquinoline-3-carbohydrazide
- 6-Bromo-N'-dodecanoyl-4-hydroxy-2-oxo-2-hydroquinoline-3-carbohydrazide
- 6-Chloro-N'-dodecanoyl-4-hydroxy-2-oxo-2-hydroquinoline-3-carbohydrazide
- 6-Bromo-4-hydroxy-1-methyl-N'-octanoyl-2-oxo-1,2-dihydroquinoline-3-carbohydrazide
- 6-Bromo-N'-dodecanoyl-4-hydroxy-1-methyl-2-oxo-1,2-dihydroquinoline-3-carbohydrazide
- 6-Bromo-1-ethyl-4-hydroxy-N'-octanoyl-2-oxo-1,2-dihydroquinoline-3-carbohydrazide
- 6-Bromo-N'-dodecanoyl-1-ethyl-4-hydroxy-2-oxo-1,2-dihydroquinoline-3-carbohydrazide
- 6-Chloro-4-hydroxy-1-methyl-N'-octanoyl-2-oxo-1,2-dihydroquinoline-3-carbohydrazide
- 6-Chloro-N'-dodecanoyl-4-hydroxy-1-methyl-2-oxo-1,2-dihydroquinoline-3-carbohydrazide
- 6-Chloro-1-ethyl-4-hydroxy-N'-octanoyl-2-oxo-1,2-dihydroquinoline-3-carbohydrazide
- 6-Chloro-N'-dodecanoyl-1-ethyl-4-hydroxy-2-oxo-1,2-dihydroquinoline-3-carbohydrazide
- 7-Chloro-4-hydroxy-1-methyl-N'-octanoyl-2-oxo-1,2-dihydroquinoline-3-carbohydrazide
- 7-Chloro-N'-dodecanoyl-4-hydroxy-1-methyl-2-oxo-1,2-dihydroquinoline-3-carbohydrazide
- 7-Chloro-1-ethyl-4-hydroxy-N'-octanoyl-2-oxo-1,2-dihydroquinoline-3-carbohydrazide
- 7-Chloro-N'dodecanoyl-1-ethyl-4-hydroxy-2-oxo-1,2-dihydroquinoline-3-carbohydrazide
- 1-Benzyl-7-chloro-4-hydroxy-N'-octanoyl-2-oxo-1,2-dihydroquinoline-3-carbohydrazide
- 1-Benzyl-7-chloro-N'dodecanoyl-4-hydroxy-2-oxo-1,2-dihydroquinoline-3-carbohydrazide.

9. The pharmaceutical composition according to claim 1, where the compound of formula (II) is selected from the following group:
- 7-Chloro-N'-dodecanoyl-4-hydroxy-2-oxo-2-hydroquinoline-3-carbohydrazide
- 6-Bromo-N'-dodecanoyl-4-hydroxy-2-oxo-2-hydroquinoline-3-carbohydrazide
- 6-Chloro-N'-dodecanoyl-4-hydroxy-2-oxo-2-hydroquinoline-3-carbohydrazide
- 6-Bromo-N'-dodecanoyl-1-ethyl-4-hydroxy-2-oxo-1,2-dihydroquinoline-3-carbohydrazide
- 6-Chloro-N'-dodecanoyl-1-ethyl-4-hydroxy-2-oxo-1,2-dihydroquinoline-3-carbohydrazide
- 7-Chloro-N'-dodecanoyl-4-hydroxy-1-methyl-2-oxo-1,2-dihydroquinoline-3-carbohydrazide
- 7-Chloro-N'-dodecanoyl-1-ethyl-4-hydroxy-2-oxo-1,2-dihydroquinoline-3-carbohydrazide.

\* \* \* \* \*